(12) United States Patent
O'Toole

(10) Patent No.: US 11,738,883 B2
(45) Date of Patent: Aug. 29, 2023

(54) EXPANDING FLOOR/ ACCORDION DRONE DOCKING STATION

(71) Applicant: Daniel S O'Toole, Carmel, IN (US)

(72) Inventor: Daniel S O'Toole, Carmel, IN (US)

( * ) Notice: Subject to any disclaimer, the term of this patent is extended or adjusted under 35 U.S.C. 154(b) by 310 days.

(21) Appl. No.: 17/233,624

(22) Filed: Apr. 19, 2021

(65) Prior Publication Data

US 2021/0394930 A1   Dec. 23, 2021

Related U.S. Application Data

(60) Provisional application No. 63/012,662, filed on Apr. 20, 2020.

(51) Int. Cl.

| | |
|---|---|
| *B64F 1/32* | (2006.01) |
| *B60L 53/80* | (2019.01) |
| *A47G 29/14* | (2006.01) |
| *A47G 29/30* | (2006.01) |
| *A61L 12/00* | (2006.01) |
| *B64F 1/36* | (2017.01) |
| *G05B 15/02* | (2006.01) |

(Continued)

(52) U.S. Cl.
CPC .............. *B64F 1/32* (2013.01); *A47G 29/141* (2013.01); *A47G 29/30* (2013.01); *A61L 12/00* (2013.01); *B60L 53/80* (2019.02); *B64F 1/362* (2013.01); *G05B 15/02* (2013.01); *A47G 2029/145* (2013.01); *A47G 2029/146* (2013.01); *A47G 2029/147* (2013.01); *A47G 2029/149* (2013.01); *A61L 2202/11* (2013.01); *B60L 2200/10* (2013.01); *F21S 10/06* (2013.01); *F21Y 2115/10* (2016.08); *G01S 19/42* (2013.01); *G06K 7/0004* (2013.01); *H02J 7/0013* (2013.01)

(58) Field of Classification Search
None
See application file for complete search history.

(56) References Cited

U.S. PATENT DOCUMENTS 9,211,025 B1   12/2015  Walid et al.
9,244,147 B1   1/2016   Soundararajan et al.
(Continued)

FOREIGN PATENT DOCUMENTS

CA            2898304 C      1/2020

*Primary Examiner* — K. Wong
(74) *Attorney, Agent, or Firm* — Ritchison Law Offices PC; John D Ritchison

(57) ABSTRACT

Disclosed herein is a drone docking station for deposit of items/goods delivered by a drone to a secured receptacle. Items can be delivered to a receptacle at a curb, mailbox, post, porch, in-ground vault, and window to a multi-parcel receptacle with an expanding floor/accordion station that has a specific residential/commercial address with various optional features. Features include communication systems between the station and drone; security; hot and cold temperature control and preservation of the goods before and after delivery; battery charging and exchange station; a collector to identify explosive materials, anthrax, etc.; ultraviolet system to eradicate disease, virus and harmful materials; an ozone applicator to eradicate disease, virus and harmful materials; weather monitoring; tag and track of vehicles and packages; facial recognition camera and software for pets and humans; and local two-way speakers; LED lights that strobe flash, and a flood light.

39 Claims, 12 Drawing Sheets

(51) Int. Cl.
*F21Y 115/10* (2016.01)
*F21S 10/06* (2006.01)
*G01S 19/42* (2010.01)
*G06K 7/00* (2006.01)
*H02J 7/00* (2006.01)

(56) References Cited

U.S. PATENT DOCUMENTS

| | | |
|---|---|---|
| 9,387,928 B1 | 7/2016 | Gentry et al. |
| 9,527,605 B1 | 12/2016 | Gentry et al. |
| 9,536,216 B1 | 1/2017 | Lisso |
| 9,650,136 B1 | 5/2017 | Haskin et al. |
| 9,840,340 B2 * | 12/2017 | O'Toole ............... G06Q 10/083 |
| 9,928,749 B2 | 3/2018 | Gil et al. |
| 9,969,495 B2 | 5/2018 | Gil et al. |
| 10,112,712 B1 | 10/2018 | Gentry et al. |
| 10,124,912 B2 | 11/2018 | Walsh et al. |
| 10,147,067 B2 | 12/2018 | Pleis |
| 10,163,177 B2 | 12/2018 | Farris et al. |
| 10,210,475 B2 | 2/2019 | Pargoe |
| 10,287,034 B2 | 5/2019 | Mozer |
| 10,373,507 B2 | 8/2019 | Marcell et al. |
| 10,457,421 B2 | 10/2019 | O'Toole |
| 10,592,843 B2 | 3/2020 | Natarajan et al. |
| 10,874,240 B2 | 12/2020 | Lewis et al. |

\* cited by examiner

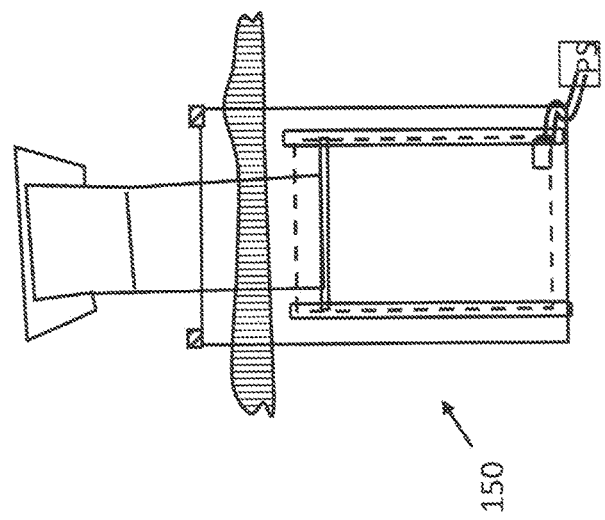
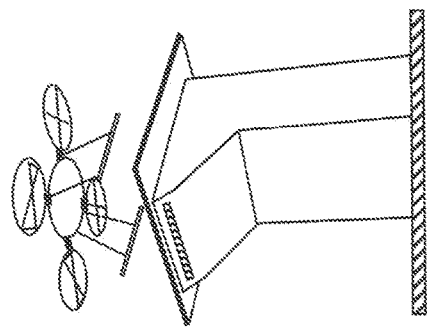
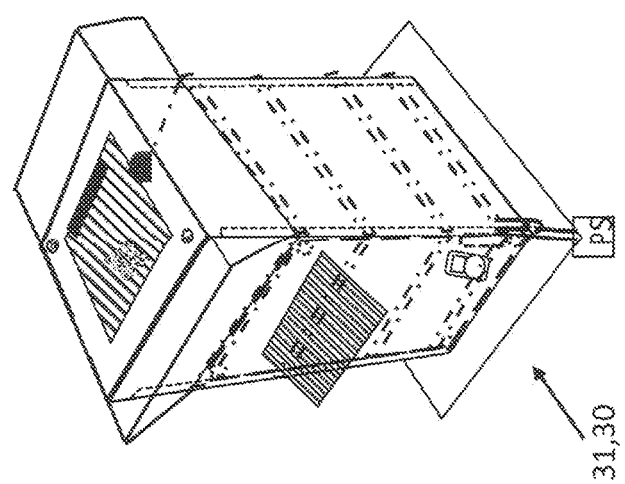
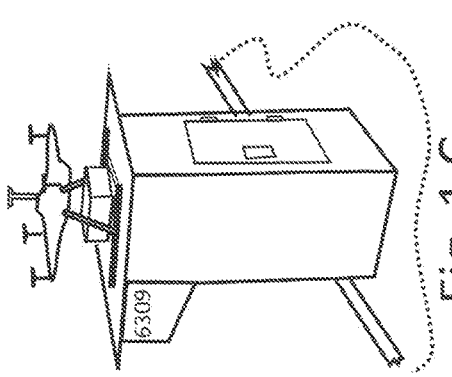
Fig. 1A
Fig. 1B
Fig. 1C
Fig. 1D

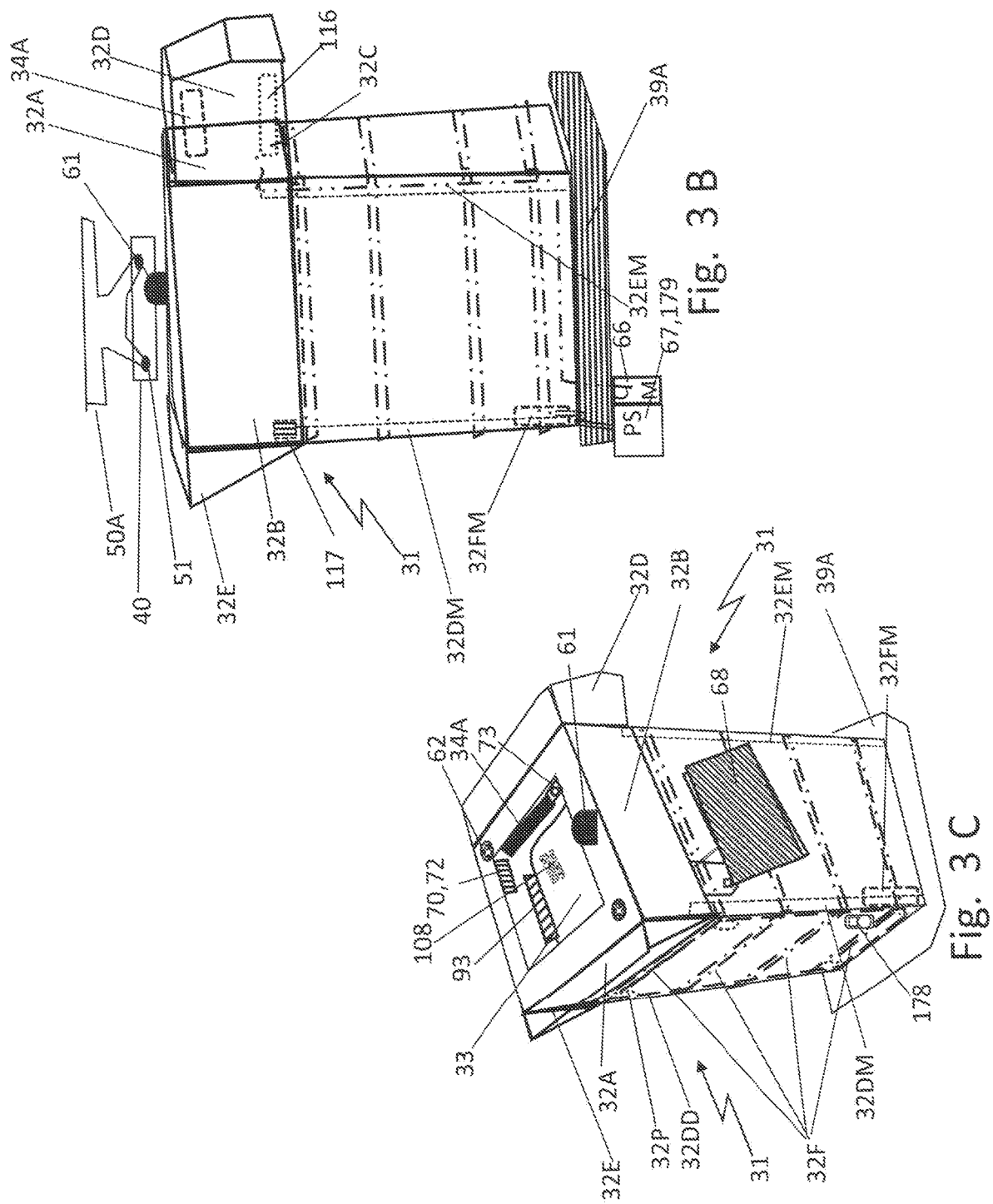

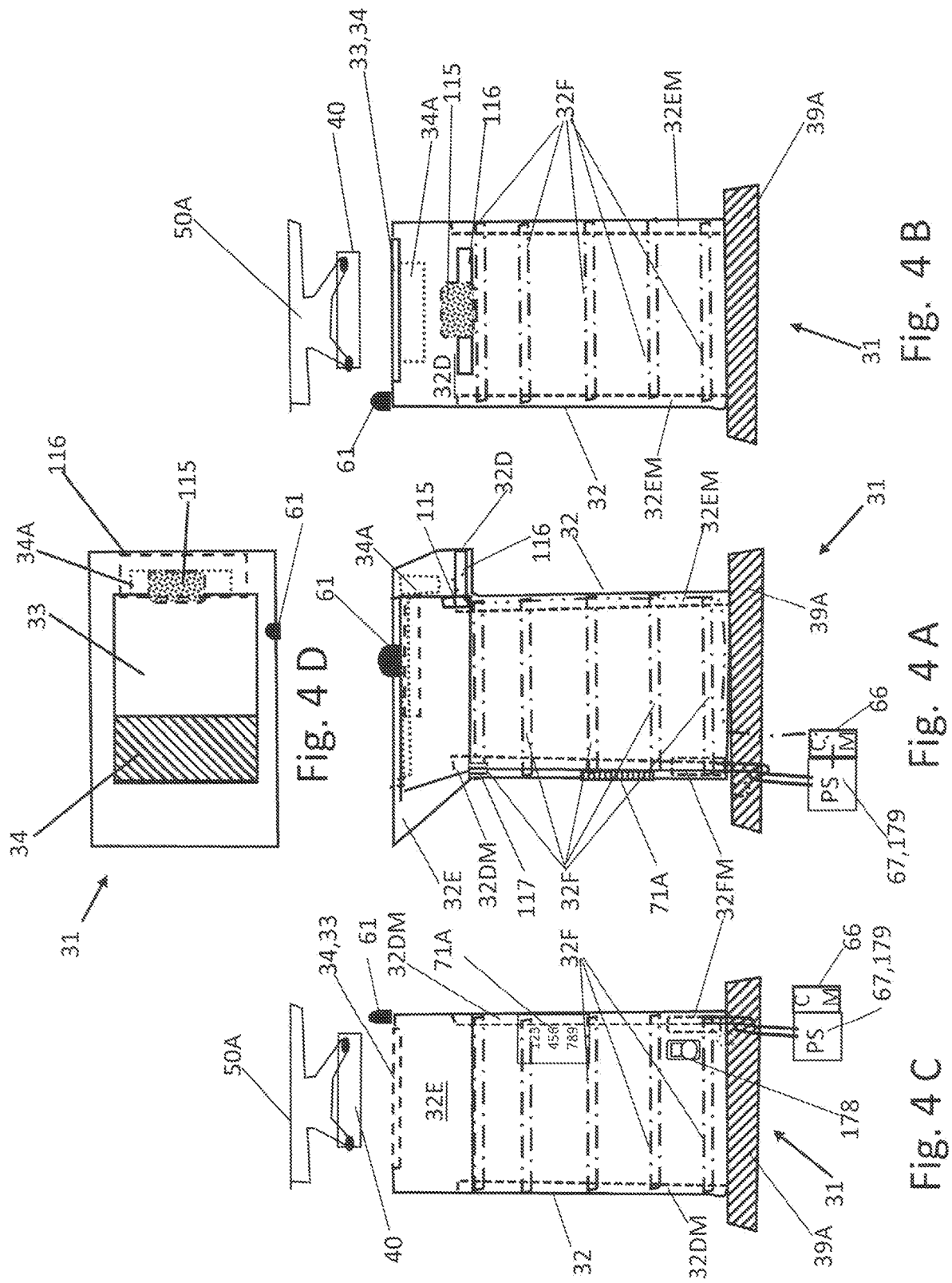

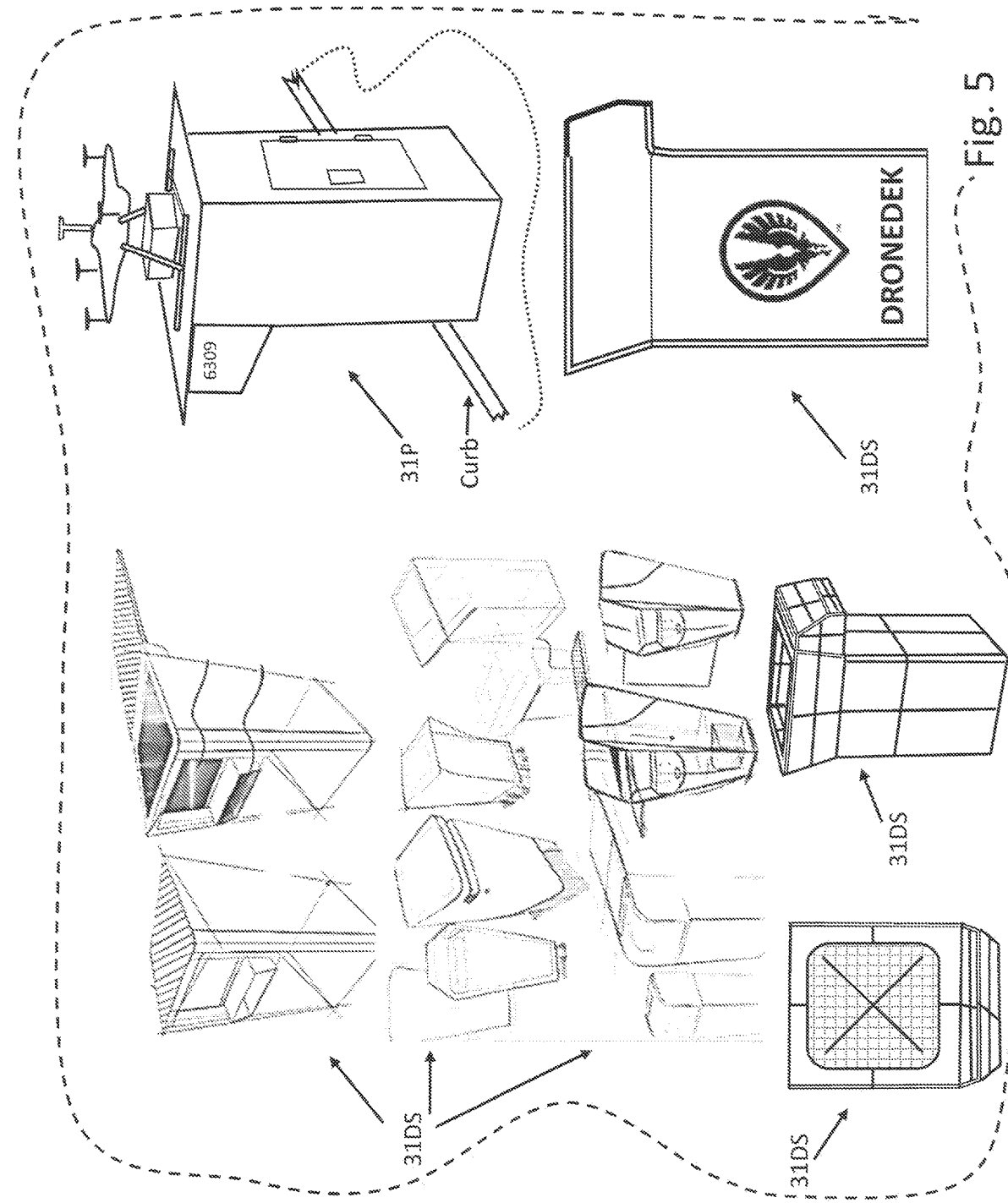

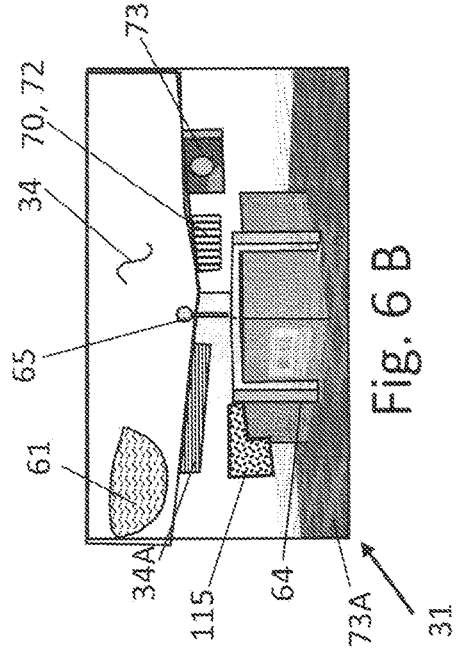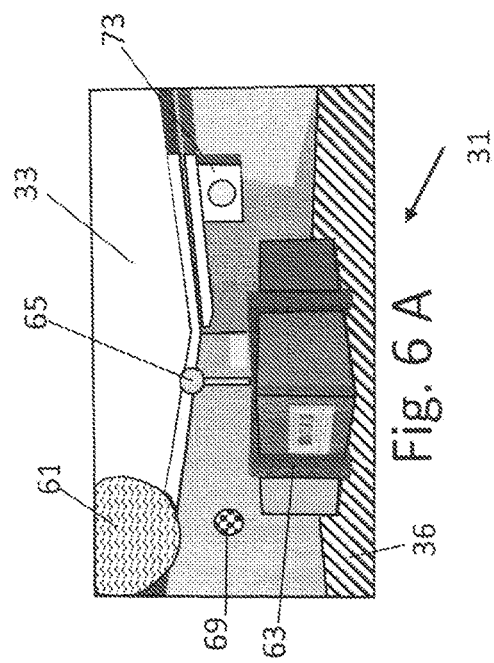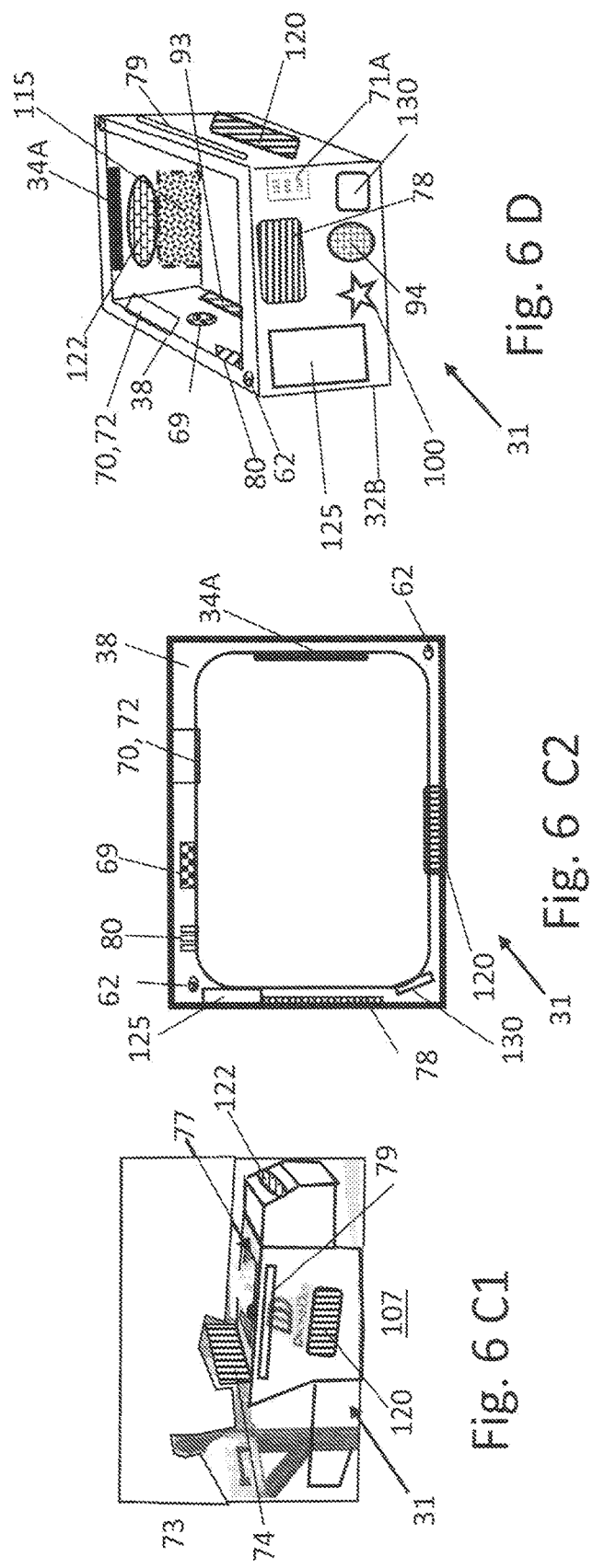

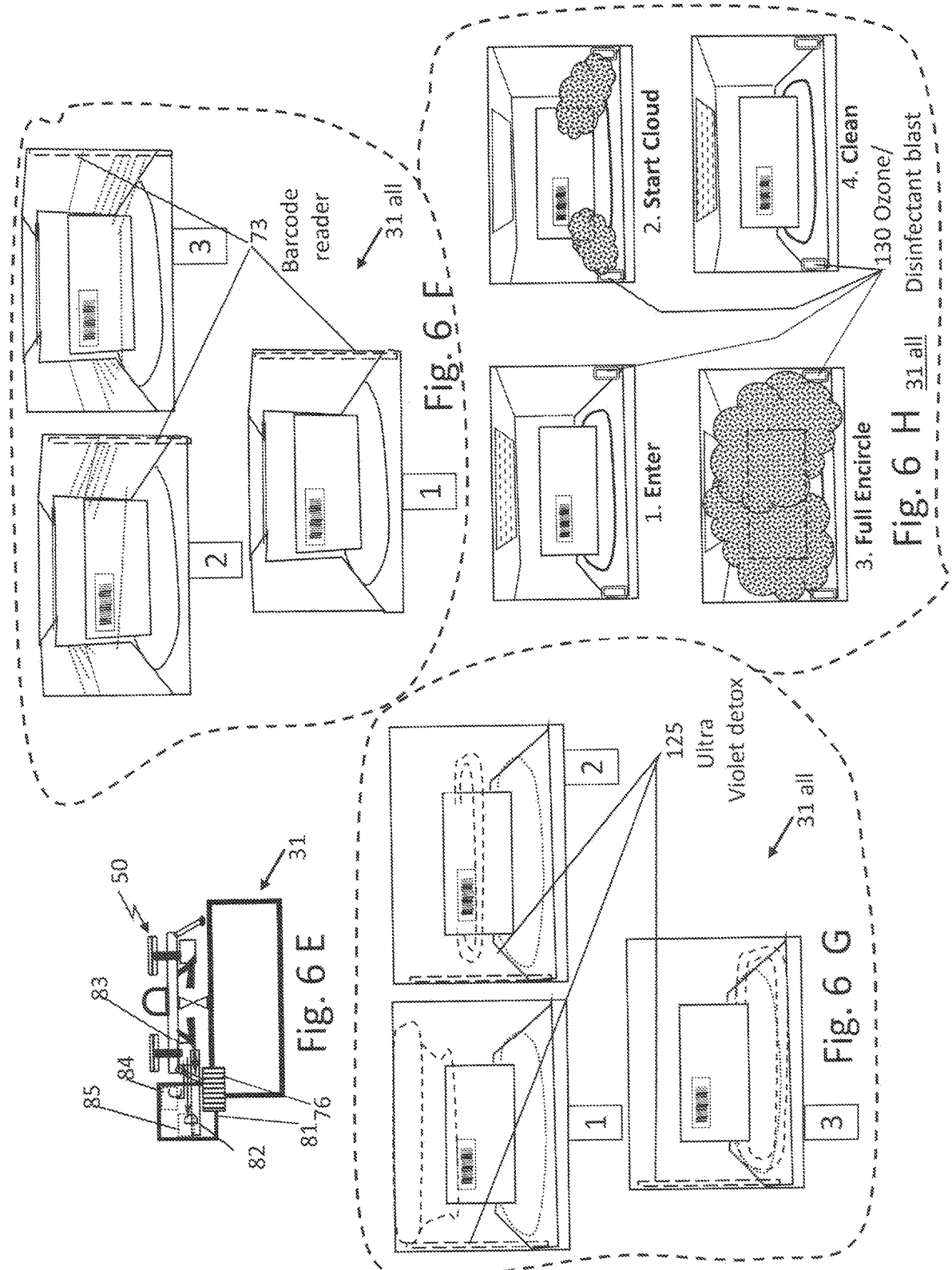

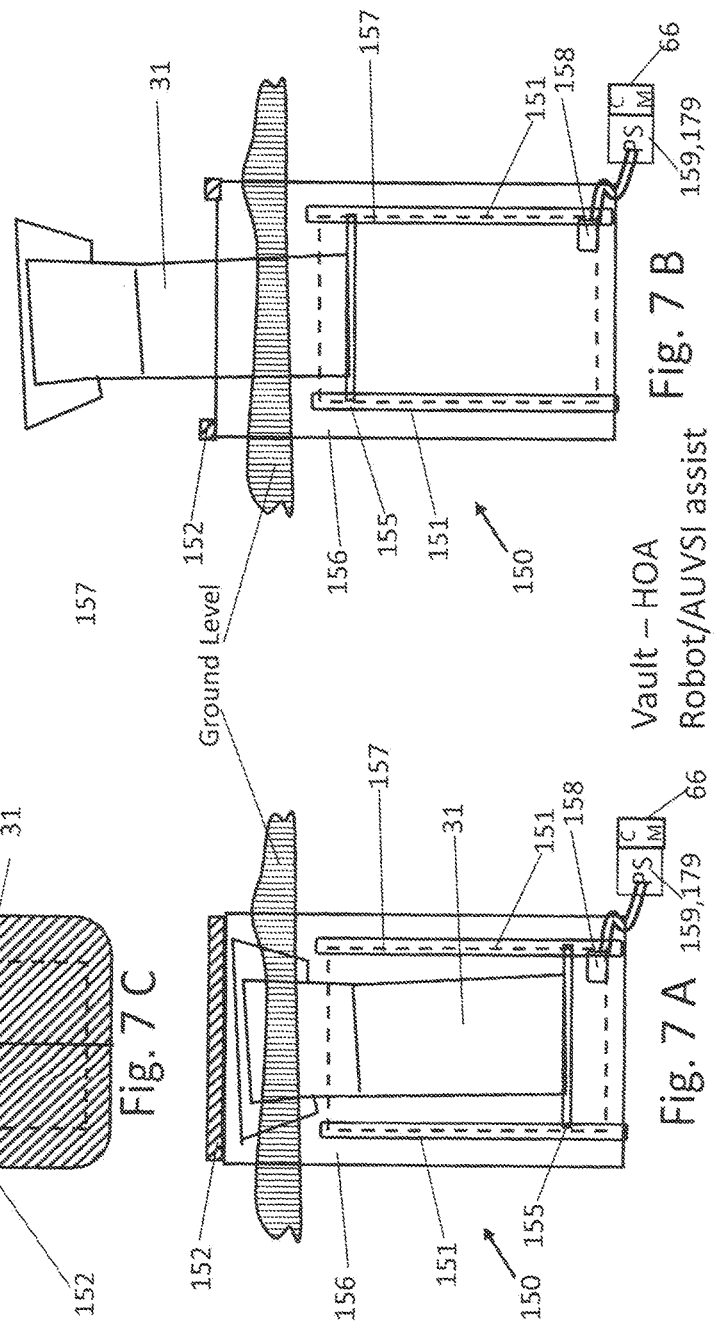

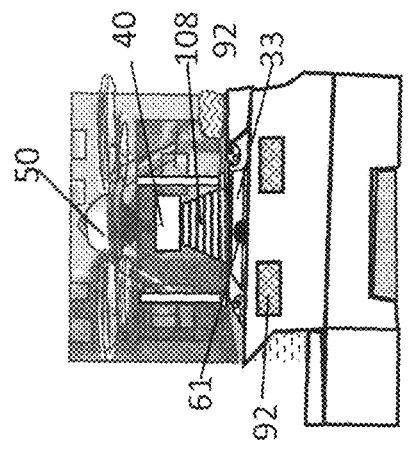
Fig. 8A
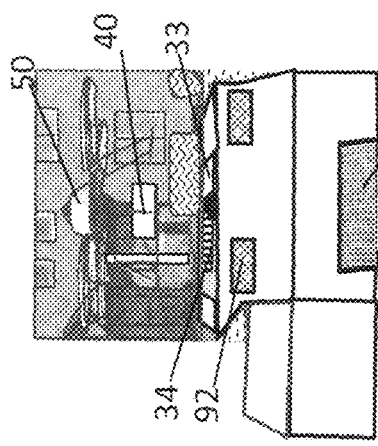
Fig. 8B
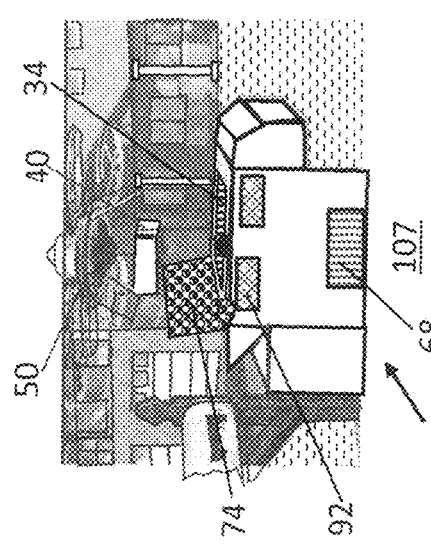
Fig. 8C
8A through 8E Replaced background photographs of housing with sketches
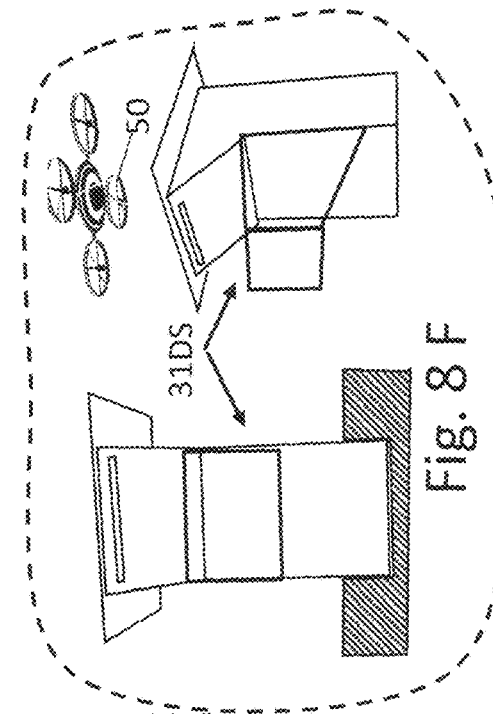
Fig. 8F
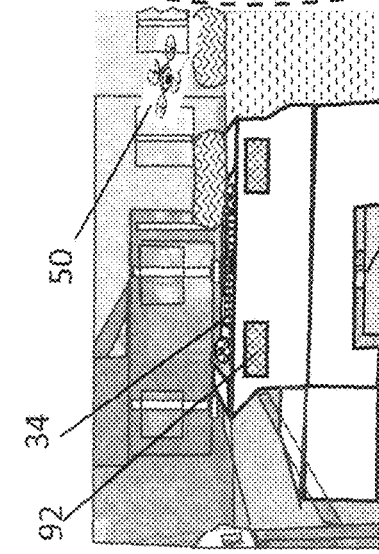
Fig. 8E
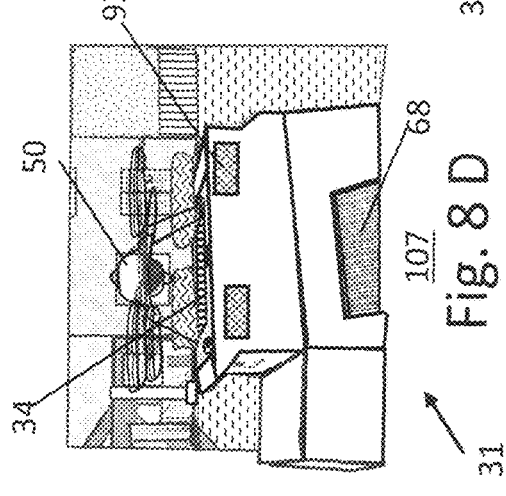
Fig. 8D

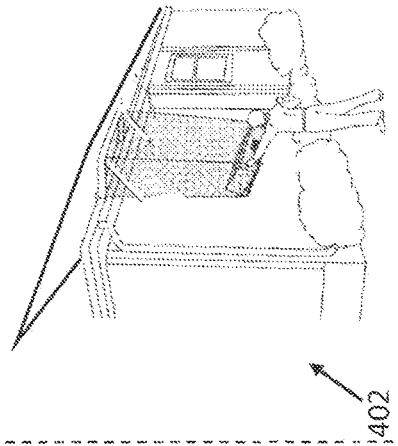
FIG. 9 B
Prior Art
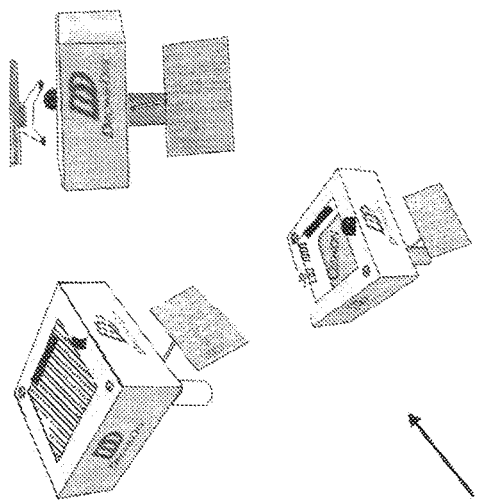
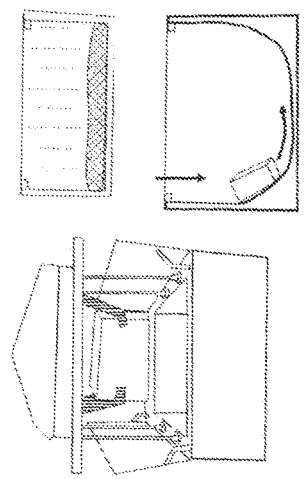
FIG. 9 A
Prior Art
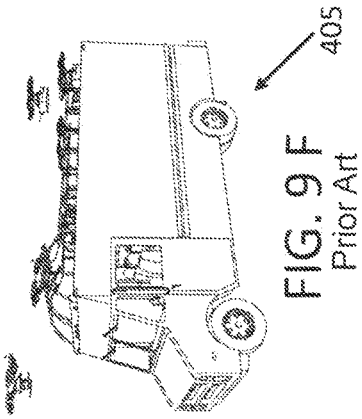
FIG. 9 C
Prior Art
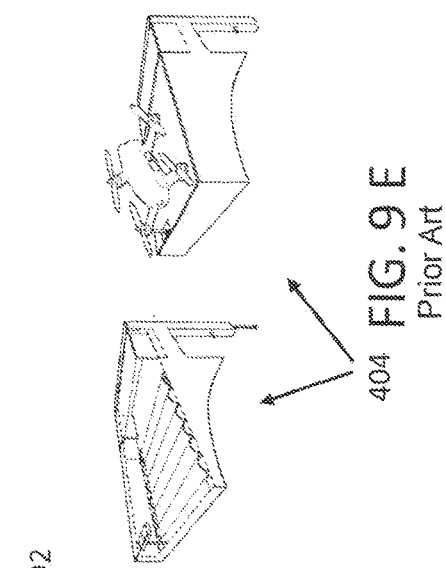
FIG. 9 F
Prior Art
FIG. 9 E
Prior Art
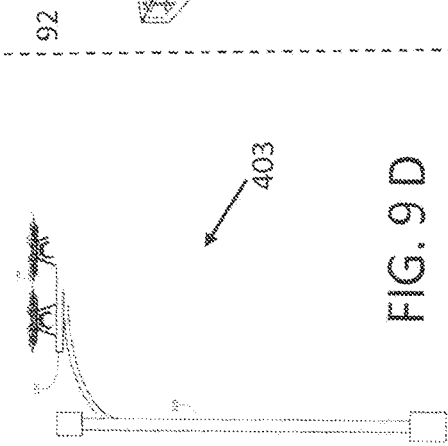
FIG. 9 D
Prior Art

EXPANDING FLOOR/ ACCORDION DRONE DOCKING STATION

CROSS-REFERENCE TO RELATED APPLICATIONS

This application claims the benefit of United States Provisional Patent Application with Ser. No. 63/012,662 filed Apr. 20, 2020, by Daniel S. O'Toole. The application was entitled a "Special Expanding Floor/Accordion drone docking station called a DRONEDEK."

FIELD OF INVENTION

This invention relates to a Special Expanding Floor/ Accordion drone docking station called a DRONEDEK. The invention relates to drones and delivery of parcels or goods. The present application relates to a delivery location for receiving a package from a vehicle—drone or unmanned aerial vehicle (UAV), robotic carriers, or automated unmanned vehicle systems (AUVS). The present disclosure relates to unmanned and drone aircraft, more specifically to landing and docking systems for unmanned aircraft to deliver o receive goods. The embodiments of the disclosure relate to the field of aircrafts and unmanned vehicular delivery, in particular to a device for receiving and sending an article. A device for a drone docking station for deposit of items delivered by drone, robot or AUVS. Items may include but not be limited to food items, groceries, and parcels. A secure porch, roof, window or otherwise building mounted box may be secured through to an existing edifice or may be configured to mount to an existing mailbox post and/or take the place of the mailbox. The invention relates to drones and delivery of parcels or goods.

FEDERALLY SPONSORED RESEARCH

None.

SEQUENCE LISTING OR PROGRAM

None.

BACKGROUND—FIELD OF INVENTION AND PRIOR ART

As far as known, there are no Special Expanding Floor/ Accordion drone docking station called a DRONEDEK or the like. It is believed that this product is unique in its design and technologies. This background as to drone deliveries and the current industry and market should be useful. Unmanned aerial vehicles (UAVs) comprise a variety of vehicles, from conventional fixed wing airplanes, to helicopters, to ornithopters (i.e., machines that fly like birds), and are used in a variety of roles. They can be remotely piloted by a pilot on the ground or can be autonomous or semi-autonomous vehicles that fly missions using preprogrammed coordinates, GPS navigation, etc. UAVs can include remote control helicopters and airplanes for the hobbyist, for example. UAVs may be equipped with cameras to provide imagery during flight, which may be used for navigational or other purposes, e.g., identify a house address, etc. UAVs can also be equipped with sensors to provide local weather and atmospheric conditions, radiation levels, and other conditions. UAVs may also include cargo bays, hooks, or other means for carrying payloads. Newer generation UAVs may also provide significant payload capabilities. As a result, UAVs can also be used for delivering packages, groceries, mail, and other items. The use of UAVs for deliveries can reduce costs and increase speed and accuracy. The range provided by current UAV technology, however, makes deliveries over a wide area—e.g., throughout a city, or even a portion of a city-difficult.

Parcel transportation between an origin and a destination is traditionally a labor-intensive process. For short distance, "local" deliveries, an item (e.g., parcel) may be transported by a delivery person between the origin and the destination. For example, the delivery person may drive a vehicle to transport the item between the origin and the destination and may ensure that the item is properly picked up and/or delivered according to delivery instructions. For longer-distance deliveries, transportation of an item may involve several delivery personnel, who may individually perform one or more steps for picking up an item, sorting the item one or more times, transporting the item from a final sort of location to a final delivery destination, and/or delivering the item from the delivery vehicle to the destination address (e.g., serviceable point). Because of the labor-intensive nature of this process, various attempts have been made to assist carrier personnel by reducing the physical demands required in the transportation and delivery process; however, prior attempts have faced substantial difficulties in ensuring that various aspects of the transportation and delivery process are properly performed. For example, attempts have been made to utilize unmanned vehicles, such as Unmanned Aerial Vehicles (UAVs) to transport items from a final sort of location to an intended delivery destination. However, such concepts are generally limited by the effective range of the UAVs, as well as the number of available UAVs that may be utilized to deliver items to locations a substantial distance away from the final sort of location. Accordingly, a need exists for additional systems and methods to assist carrier personnel and thereby reduce the physical demands of the transportation and delivery process.

Typically ordered items are packed in shipping packages (e.g., corrugated boxes) and shipped to the user's residence or place of business. Physical delivery of items to user specified locations has improved dramatically over the years, with some retailers offering next day delivery of ordered items. The final or last mile delivery of physical items to a user specified location is traditionally accomplished using a human controlled truck, bicycle, cart, etc. For example, a user may order an item for delivery to their home. The item may be picked from a ground-based material handling facility, packed, and shipped to the user for final delivery by a shipping carrier. The shipping carrier will load the item onto a truck that is driven by a human to the final delivery location and the human driver, or another human companion with the driver, will retrieve the item from the truck and complete the delivery to the destination. For example, the human may hand the item to a recipient, place the item on the user's porch, store the item in a post office box, etc. In these new times where the world is changing before ones very eyes, technology must keep up with consumer habits. Efficiency, cost savings, technology, convenience, ease, safety, and more combine to dictate where the US and world market economy is going.

One emerging sector of the economy is last mile logistics. Within this segment of the shipping economy is a rapidly developing facet known as drone delivery. Shifting metrics in the world's ecosystem dictate now, more than ever, the need for autonomous delivery. Enter DRONEDEK. DRONEDEK currently holds two US Utility Patents, and it continues to constantly build on its offerings. Every day in the US 1.7 million packages is stolen. The loss created is in the billions. DRONEDEK solves this problem through encrypted, authenticated delivery. Every day in the US, thousands of packages are mis-shipped. DRONEDEK solves this problem through encrypted, authenticated delivery. In this new world, social distancing will be the "new normal". DRONEDEK allows shippers, deliverers, and recipients to practice social distancing all while increasing the user experience.

Millennials are a growing force in the US and world economy, and they have their own way of doing things. More and more people are working from home, venturing out less and expecting "the away from home" experience at home. Enter DRONEDEK. DRONEDEK brings so many features and benefits to the user experience all while delivering more. In addition to the demands mentioned above, the consumer wants their purchases now. DRONEDEK is a vital component in the emerging drone delivery economy. Delivering items quicker and cheaper by way of drone, autonomous driverless vehicle or robot only solves part of the problem. If those items are not delivered to a safe, smart, secure receptacle, everything gained in the process is lost at the front door. Parcel delivery is the fastest growing segment in delivery commerce. DRONEDEK will accelerate the timing for it to happen. Additionally, DRONEDEK will open other facets of delivery through autonomous vehicles. Food, beverage, and pharmaceutical delivery will all benefit through the DRONEDEK platform.

The market includes all residential and commercial street addresses in the USA. Each day 100M items are purchased on the internet of which 91% of the e-commerce deliveries are less than 5 lbs which matches the typical drone weigh capacity and fits within DRONEDEK's cargo bay that measures 24 by 24 inches in diameter. The market for secured drone receptacle will grow exponentially as demonstrated by retail statistics showing the accelerating trend of online commerce and coupled with the even faster growth of unsecured conventional delivery theft or porch piracy. The USPS reported that 1.7M USPS packages are being stolen each day, enhancing DRONDEK's market relevance and demand for its smart secured drone delivery solution. Shippers today incur an estimated $2 per delivery costs while drone delivery is estimated to generate $1 cost saving per delivery for the logistics industry. As a result, DRONEDEK's business model and smart mailbox delivers a disruptive savings to the logistics industry of $1 Billion every 11 days.

Problem Solved

The improvement and problem solved as a device for an expanded drone docking stations are several: the Special Expanding Floor/Accordion drone docking station called a DRONEDEK provides expanded volume for several packages and deliveries to the on docking station; it administers Ultraviolet or ozone disinfecting/detoxing to remove infectious disease, viruses and bacteria; it provides inter-communication to other drones, UAVs, AUVS, and robots delivering in the area; it serves as a weather monitoring station, traffic, human and pet movement with facial recognition cameras, as well as able to tag and track for authorities; it interchanges information with providers and collects information for Big Data Collection and Networking for marketing information and data; at the location of the DRONEDEK docking station it provides flood lights, two way speakers, alarms, and flashing and colored lighting for security and communications; it accommodates a ground vault for meeting homeowner association rules and restrictions; it monitors weight and size of package and can tattoo brand packages for returns; it has an assist mechanism for robot/AUVS (automated unmanned vehicle systems) assist to unload of parcels to DRONEDEK; and it has an assist for and it can provide a charging station or battery exchange to the drones and UAVs.

PRIOR ART

A novelty search revealed no other prior art that conflicts with this Special Expanding Floor/Accordion drone docking station called a DRONEDEK. The prior art found included:

A. U.S. Pat. No. 9,211,025 called a Postal cube and issued in 2015 to Walid and Elhawashy describes a device configured to securely and automatically receive parcel is described. The device is equipped with a front door and an automatic top rolling door in order to accommodate parcel delivery via conventional parcel delivery personnel, or delivery via airlift from an unmanned aerial vehicle (UAV). The device is also equipped with a secure internet connection which facilitates communication between recipient and delivery personnel, as well as expedites the delivery confirmation process upon parcel delivery. Audio and video capture and transmission equipment on-board the device permit the recipient to remotely provide access to the device upon authentication of identity and/or credentials.

B. U.S. Pat. No. 9,244,147 called an Automated package delivery to a delivery receptacle issued to Soundararajan et al. and assigned to Google Wings which was issued in 2016 teaches improving automated package delivery to mobile delivery receptacles to allow accurate and reliable package deliveries comprises a delivery receptacle for an automated package delivery via an unmanned aerial delivery device. The delivery receptacle is notified of a pending delivery and travels to a receiving location. The delivery receptacle emits infrared ("IR") beacons from one or more IR beacon transmitters. An aerial delivery device detects the IR beacon and uses the beacons to navigate to the delivery receptacle. The delivery receptacle receives IR beacon responses from the aerial delivery device and continually or periodically directs the IR beacons in the direction of the aerial delivery device. The aerial delivery device deposits the package in the delivery receptacle. After receiving the package, the delivery receptacle transports the package to a secure location, such as into a garage.

C. U.S. Pat. No. 984,034 called a Drone docking station and delivery system and issued in 2017 to Dan O'Toole (Licensed to DRONEDEK Corporation teaches a drone docking station for deposit of items delivered by drone. Items may include food items, groceries, parcels, and others. A secure porch, roof, window or otherwise building mounted box may be secured through to an existing edifice or may be configured to mount to an existing mailbox post. The basic elements making up the components of the box enable it to carry out efficient and secure delivery of goods to a container box located at a specific address and to securely hold those goods until they are picked-up regardless of duration, weather, or otherwise. The drone dock may employ different technological devices to provide for communication between the drone docking station and a drone to provide security and preservation of the delivered goods before during and after delivery.

D. U.S. Pat. No. 9,387,928 called a Multi-use UAV docking station systems and methods issued in 2016 to Gentry, et al and assigned to Amazon Tech portrays a systems and methods for providing a series of multiuse UAV docking stations are disclosed. The docking stations can be networked with a central control and a plurality of UAVs. The docking stations can include a number of services to facilitate both UAV guidance and maintenance and community acceptance and benefits. The docking stations can include package handling facilities and can act as a final destination or as a delivery hub. The docking stations can extend the range of UAVs by providing recharging/refueling stations for the UAVs. The docking stations can also include navigational aid to guide the UAVs to the docking stations and to provide routing information from the central control. The docking stations can be incorporated into existing structures such as cell towers, light and power poles, and buildings. The docking stations can also comprise standalone structures to provide additional services to underserved areas.

E. U.S. Pat. No. 9,527,605 called a Multi-use, unmanned aerial vehicle docking station issued in 2016 to Gentry, et al and assigned to Amazon Tech teaches a systems and methods for providing a series of multiuse UAV docking stations. The docking stations can be networked with a central control and a plurality of UAVs. The docking stations can include a number of services to facilitate both UAV guidance and maintenance and community acceptance and benefits. The docking stations can include package handling facilities and can act as a final destination or as a delivery hub. The docking stations can extend the range of UAVs by providing recharging/refueling stations for the UAVs. The docking stations can also include navigational aid to guide the UAVs to the docking stations and to provide routing information from the central control. The docking stations can be incorporated into existing structures such as cell towers, light and power poles, and buildings. The docking stations can also comprise standalone structures to provide additional services to underserved areas.

F. U.S. Pat. No. 9,536,216 named and called a Delivery of packages by unmanned aerial vehicles was issued in 2017 to Lisso and assigned to Amazon Tech. It shows a package delivery apparatus uses an unmanned aerial vehicle (UAV) to deliver a package containing a product to a delivery destination area. The UAV uses GPS signals to guide it to the delivery destination area and an altimeter to determine its height above the delivery destination area. The UAV then adjusts its height to a preferred drop or release height for that package and product and releases the package. An optional camera allows a human operator to view the delivery destination area. An expandable foam package surrounds the product to protect the product from impact and moisture. The package may be streamlined to reduce air resistance and increase the range of the UAV. The package characteristics, such as its thickness, are determined based one or more of the weight and fragile nature of the product, and the drop height.

G. U.S. patent Ser. No. 10/124,912 called a Landing Pad for Unmanned Aerial Vehicle Delivery that was issued in 2018 with a disputed prior submission and to Walsh et al. and assigned to Valqari is described as a landing pad receives and stores packages delivered from an aerial vehicle are awaiting pickup from an aerial vehicle. The landing pad can be placed outside of a window and can contain a transmitter for sending out an identification signal via radio frequency to aid aerial vehicles in finding the landing pad. The landing pad contains a landing platform with a trapdoor that leads to a storage compartment. The trapdoor can be configured to only open when it receives a signal from an authorized aerial vehicle. The storage compartment can be accessed via a storage compartment door which can contain a locking mechanism. The storage compartment can be climate controlled. The landing pad can also have a transmitter that emits sounds to discourage animals from nesting on or near the landing pad. The landing pad can also include a solar power generator as a source of electrical energy.

H. U.S. Pat. No. 9,650,136 is named an Unmanned aerial vehicle payload delivery and was issued in 2017 to Haskin et al and assigned to Amazon Tech. It provides techniques for using an unmanned aerial vehicle (UAV) to deliver a payload may be provided. For example, upon arrival to a delivery location, the UAV may release the payload and lower a tether coupling the payload to the UAV. Based on a distance associated with the lowering of the payload, the UAV may release the cable. This release may decouple the payload and at a least a portion of the cable from the UAV, thereby delivering the payload at the delivery location.

I. U.S. patent Ser. No. 10/163,177 is entitled a System and method for controlling drone delivery or pick up during a delivery or pick-up phase of drone Operation was issued in 2018 to Ferris & McGee. It describes a system including a landing location where a drone at least one of delivers and acquires a parcel, and a homing device to interact with the drone to guide the drone to the landing location independent of interaction from another source. The homing device guides the drone during the landing phase of a flight plan. A method is also disclosed.

J. U.S. Pat. No. 9,928,749 named a Methods for delivering a parcel to a restricted access area was issued in 2018 to Gil et al. and assigned to UPS. It teaches a systems and methods include UAVs that serve to assist carrier personnel by reducing the physical demands of the transportation and delivery process. A UAV generally includes a UAV chassis including an upper portion, a plurality of propulsion members configured to provide lift to the UAV chassis, and a parcel carrier configured for being selectively coupled to and removed from the UAV chassis. UAV support mechanisms are utilized to load and unload parcel carriers to the UAV chassis, and the UAV lands on and takes off from the UAV support mechanism to deliver parcels to a serviceable point. The UAV includes computing entities that interface with different systems and computing entities to send and receive various types of information.

K. U.S. patent Ser. No. 10/457,421 called a Drone docking station and delivery system was issued in 2019 to Dan O'Toole and licensed to DRONEDEK Corporation. It discloses a system and device for a drone docking station for deposit of items delivered by drone. Items may include but not be limited to food items, groceries, and parcels. A secure porch, roof, window or otherwise building mounted box may be secured through to an existing edifice or may be configured to mount to an existing mailbox post and actually take the place of the mailbox. The basic elements making of components of the box enable it to carry out one efficient and secure delivery of goods to a container box located at a specific address, and to securely hold those good until they are picked up regardless of duration, weather, or otherwise. The drone dock may employ many different technological devices in order to provide for communication between the drone dock and a drone, security, and preservation of the delivered goods before during and after delivery.

Continuing with prior art:

L. U.S. patent Ser. No. 10/210,475 named a Systems, Devices, and/or Methods for Managing Drone Deliveries was issued in 2019 to Pargoe and assigned to Airbox. It describes a certain exemplary embodiments can provide an AirBox constructed to receive deliveries from a drone. The AirBox can comprise an automatically openable lid; and a wireless receiver that is constructed to receive data concerning a delivery from the drone. The automatically openable lid can open to receive the delivery from the drone.

M. A U.S. patent Ser. No. 10/373,507 describes and names a Multi-functional motorized box and landing pad for automatic drone package delivery which issued in 2019 for Marcell et al. as assigned to Quantum Systems. This teaches an actuated box and navigation aid for automatic delivery by unmanned vehicles (UAV) or drones. It also incorporates delivery information via the web linking orders, enclosure status, package specific drone homing signals, delivery confirmations and more. This system incorporates a novel and effective means for providing a standardized and predicable area for safe landing during delivery by functionalized drones. It also secures the package from theft, vandalism, animals, and the weather and provides features necessary for air-traffic management.

N. U.S. patent Ser. No. 10/287,034 is a Drone aircraft landing and docking systems issued in 2019 to Mozer and assigned to American Robotics, Inc. It describes a docking station for an aircraft includes a base portion and an alignment system disposed on the base portion configured to orient the aircraft relative to the base portion. The alignment system can include a plurality of protrusions extending away from the base portion in a vertical direction. The plurality of protrusions can extend away from the base portion in both the vertical direction and a horizontal direction such that the protrusions can extend from the base portion at an angle.

O. U.S. patent Ser. No. 10/112,712 is entitled a Multi-use UAV Docking Station Systems and Methods that was issued in 2018 to Gentry et al and assigned to Amazon Tech. It discusses systems and methods for providing a series of multiuse UAV docking stations are disclosed. The docking stations can be networked with a central control and a plurality of UAVs. The docking stations can include a number of services to facilitate both UAV guidance and maintenance and community acceptance and benefits. The docking stations can include package handling facilities and can act as a final destination or as a delivery hub. The docking stations can extend the range of UAVs by providing recharging/refueling stations for the UAVs. The docking stations can also include navigational aid to guide the UAVs to the docking stations and to provide routing information from the central control. The docking stations can be incorporated into existing structures such as cell towers, light and power poles, and buildings. The docking stations can also comprise standalone structures to provide additional services to underserved areas.

P. U.S. patent Ser. No. 10/147,067 issued as a Drone Operated Delivery Receptacle in 2018 to James Pleis teaches a drone operated delivery receptacle for receiving packages. The delivery receptacle includes a housing having a base, sidewalls, and an open upper end, defining an interior volume. The open upper end includes one or more gates that are movable between an open and closed configuration, and are configured to open when a delivery drone is detected by a control unit of the delivery receptacle. Preferably, the one or more gates are configured to automatically open when a drone is detected so as to allow the drone to deposit the package therein. A front wall of the housing comprises one or more doors thereon that allow the user to access the interior volume of the housing to retrieve the package therein.

Q. U.S. patent Ser. No. 10/592,843 is named an Unmanned aerial delivery to secure location and was issued in 2020 to Natarajan et al. and assigned to Walmart Apollo. This taught a delivery management system comprises a communication device that receives a notification of a communication established between an unmanned aerial vehicle (UAV) that delivers a payload and a delivery box constructed and arranged to receive the payload from the UAV when the UAV is a predetermined distance from the delivery box and moving in a direction toward the delivery box, the communication including an identity of the UAV; a verification device that processes the notification and validates the identity of the UAV; and an instruction generator that generates an instruction to the delivery box to open the delivery box in response to the verification device validating the identity of the UAV and a determination by the communication device that the communication is established between the UAV and the delivery box. The communication device includes an auto-locker communication device that outputs the instruction to the delivery box.

R. U.S. Pat. No. 9,928,749 is named a Methods for delivering a parcel to a restricted access area. Issued in 2018 to Gil et al. and assigned to UPS it shows a systems and methods include UAVs that serve to assist carrier personnel by reducing the physical demands of the transportation and delivery process. A UAV generally includes a UAV chassis including an upper portion, a plurality of propulsion members configured to provide lift to the UAV chassis, and a parcel carrier configured for being selectively coupled to and removed from the UAV chassis. UAV support mechanisms are utilized to load and unload parcel carriers to the UAV chassis, and the UAV lands on and takes off from the UAV support mechanism to deliver parcels to a serviceable point. The UAV includes computing entities that interface with different systems and computing entities to send and receive various types of information.

S. U.S. Pat. No. 9,969,495 is called an Unmanned aerial vehicle pickup and delivery systems and was issued to Gil in 2018 and assigned to UPS. This teaches a systems and methods include UAVs that serve to assist carrier personnel by reducing the physical demands of the transportation and delivery process. A UAV generally includes a UAV chassis including an upper portion, a plurality of propulsion members configured to provide lift to the UAV chassis, and a parcel carrier configured for being selectively coupled to and removed from the UAV chassis. UAV support mechanisms are utilized to load and unload parcel carriers to the UAV chassis, and the UAV lands on and takes off from the UAV support mechanism to deliver parcels to a serviceable point. The UAV includes computing entities that interface with different systems and computing entities to send and receive various types of information.

T. U.S. patent Ser. No. 10/874,240 is named a Landing pad receptacle for package delivery and receipt which was issued to in 2020 to Lewis et al. and assigned to Walmart Apollo. This describes a landing pad receptacle receives and stores a package delivered by an unmanned vehicle, comprising: a housing; a storage compartment in the housing; and a validation device that detects a presence of a package delivered by an unmanned vehicle in the storage compartment and authenticates a package for return by an unmanned vehicle.

U. Korean patent KR10196425 issued in South Korea is named a Drone delivery mailbox that issued in 2019 to Noh Hyeong in Canada. It is named a Multifunctional motorized box and landing pad for automatic drone package delivery. This was issued in 2020 and assigned to Quantum Systems Inc. It describes an actuated box and navigation aid for automatic delivery by unmanned vehicles (UAV) or drones. It also incorporates delivery information via the web linking orders, enclosure status, package specific drone homing signals, delivery confirmations and more. This system incorporates a novel and effective means for providing a standardized and predicable area for safe landing during delivery by functionalized drones. It also secures the package from theft, vandalism, animals, and the weather and provides features necessary for air-traffic management.

V. Canadian Patent CA2898304C issued in 2020 and assigned to Quantum and called the invention consists of an actuated box and navigation aid for automatic delivery by unmanned vehicles (UAV) or drones. It also incorporates delivery information via the web linking orders, enclosure status, package specific drone homing signals, delivery confirmations and more. This system incorporates a novel and effective means for providing a standardized and predicable area for safe landing during delivery by functionalized drones. It also secures the package from theft, vandalism, animals, and the weather and provides features necessary for air-traffic management.

As can be observed, none of the prior art has anticipated or caused one skilled in the art of drone docking stations to see this invention by Daniel S. O'Toole as obvious to a person skilled in the ordinary art of a docking station or delivery receptacle for drones or unmanned aerial vehicles (UAV), robotic carriers, or automated unmanned vehicle systems (AUVS). It provides a superior system for handling packages and delivering them to residential and commercial location in an effective, efficient, and safe manner.

SUMMARY OF THE INVENTION

This invention is a Special Expanding Floor/Accordion drone docking station called a DRONEDEK. The preferred embodiment of Special Expanding Floor/Accordion drone docking station called a DRONDEK is: A drone dock and delivery box for accepting drone deliveries comprising: (a) a means and structure for expanding the receiving section for containing multiple parcels with a raiseable floor; (b) means of locating the drone dock such that the drone may accurately approach and dock with the drone dock; (c) a means of engaging the drone dock such that a stable connection or attachment can be made; (d) a means of transferring the contents of the drone to the interior of the drone dock; (e) a means of preserving such as temperature control and a means for securely storing the delivered goods once in the drone dock; (f) a mean of disengaging (release) from the drone dock; (g) a means of communication between the drone and the drone dock, either directly or through a remote server; (h) a set of functional components incorporated within the box to allow for preservation and security of the stored goods, and to prevent damage during the transfer and or subsequent storage (soft); (i) a means of securing the box to a structure at a residential or commercial address; (j) a set of optional features comprising a charging station and exchange mechanism; a collector to identify explosive material, anthrax and the like; an ultraviolet scan system to eradicate disease, virus and harmful materials; an ozone applicator to eradicate disease, virus and harmful materials; (k) a set of identification feature such as a barcode reader, a weight and dimension sensor, and a tattoo printer for return parcels; (l) a set of features on the drone dock for weather monitoring, tag and track vehicles and packages, etc., and a camera with facial recognition software to track humans and pets; and (m) a set of local features such as two-way speakers, LED light that are colored and can strobe flash, and a flood light.

Objects and Advantages

There are several objects and advantages of the Special Expanding Floor/Accordion drone docking station called a DRONEDEK. There are currently no known drone docking stations or receivers for drone or unmanned aerial vehicle (UAV), robotic carriers, or automated unmanned vehicle systems (AUVS) that are effective at providing the objects of this invention. The various advantages and benefits are:

| Item | Advantages |
| --- | --- |
| 1 | Has a secure opening and closing door feature that allows the drone to communicate with the station and open and close its cargo doors to receive and ship its contents - means for locking and a keypad for onsite access to the DRONEDEK; |
| 2 | Provides expanded volume for several packages and deliveries to the on-docking station that is a secure receptacle designed to hold parcels that are received or that are waiting to be shipped accompanied with a barcode reader, a return tattoo printer for package return and ability to place gate code for manual intervention and delivery; |
| 3 | Administers Ultraviolet or ozone disinfecting/ detoxing to remove infectious disease, viruses, and bacteria; |
| 4 | Provides explosive materials and anthrax, etc. detection; |
| 5 | Provides inter-communication to other drones, UAVs, AUVS, and robots delivering in the area; |
| 6 | Serves as a weather monitoring station, traffic, human and pet movement with facial recognition cameras, as well as able to tag and track for authorities; |
| 7 | Interchanges information with providers and collects information for Big Data Collection and Networking for marketing information and data; |

| Item | Advantages |
|---|---|
| 8 | At the location of the DRONEDEK docking station it provides flood lights, two-way speakers, dog whistle, alarms, and flashing and colored lighting for security and communications; |
| 9 | Accommodates a ground vault for meeting homeowner association rules and restrictions; |
| 10 | Monitors weight and size of package and can tattoo brand packages for returns; |
| 11 | Can provide a charging station or battery exchange to the drones and UAVs; |
| 12 | Has an assist mechanism for robot/AUVS (automated unmanned vehicle systems) assist to unload of parcels to DRONEDEK; |
| 13 | Has remote access and connectivity with a contents-sensing switch that via its phone application; |
| 14 | Has a means of preserving and temperature control for the goods and deliveries of parcels; |
| 15 | Has a camera system internal/external to compartment of drone dock with technology and recognition precision to interconnect to applications for facial recognition of humans and pets and paint/tag and track monitoring communications; |
| 16 | Is powered by a solar panel and/or 110-volt electrical power supply, allowing for operation of its high-level features and a solar panel as a power source; |
| 17 | Protects packages from rain, wind, sleet, hail and snow, and harsh temperatures and a heated cargo door option allows for access during the iciest of weather; and |
| 18 | Allows through a GPS beacon for the shipping drone to home in on the DRONEDEK's precise location. |

Finally, other advantages and additional features of the present Special Expanding Floor/Accordion drone docking station called a DRONEDEK device will be more apparent from the accompanying drawings and from the full description of the device. For one skilled in the art of drone docking stations and delivery receptacles, it is readily understood that the features shown in the examples with this product are readily adapted to other types of drone docking stations and systems and devices interfacing with drone or unmanned aerial vehicle (UAV), robotic carriers, or automated unmanned vehicle systems (AUVS).

DESCRIPTION OF THE DRAWINGS—FIGURES

The accompanying drawings, which are incorporated in and constitute a part of this specification, illustrate an embodiment of the Special Expanding Floor/Accordion drone docking station called a DRONEDEK for various applications device that is preferred. The drawings together with the summary description given above and a detailed description given below explain the principles of the DRONEDEK device. It is understood, however, that the Special Expanding Floor/Accordion drone docking station called a DRONEDEK is not limited to only the precise arrangements and instrumentalities shown.

FIGS. 1A through 1D are sketches of the general drone docking station/DRONEDEK for deposit of items delivered by drone hereinafter referred to as expanded floor/and receiving section drone dock or docking station.

FIGS. 3A through 3C are sketches of a docking station/DRONEDEK with the expanding section with the components and features shown from generally a side or end view.

FIGS. 4A through 4D FIGS. are more sketches of a docking station/DRONEDEK with the expanding section with the components and features shown from several views.

FIG. 5 is a group of sketches and prototype of a docking station/DRONEDEK with the expanding section.

FIG. 6A through 6N are sketches of a general embodiment indicating some of the features of the DRONEDEK.

FIG. 7A through 7E are sketches of an inground vault system for homeowner associations and an assist mechanism for unloading robot/AUVS (automated unmanned vehicle systems).

Figure 8:
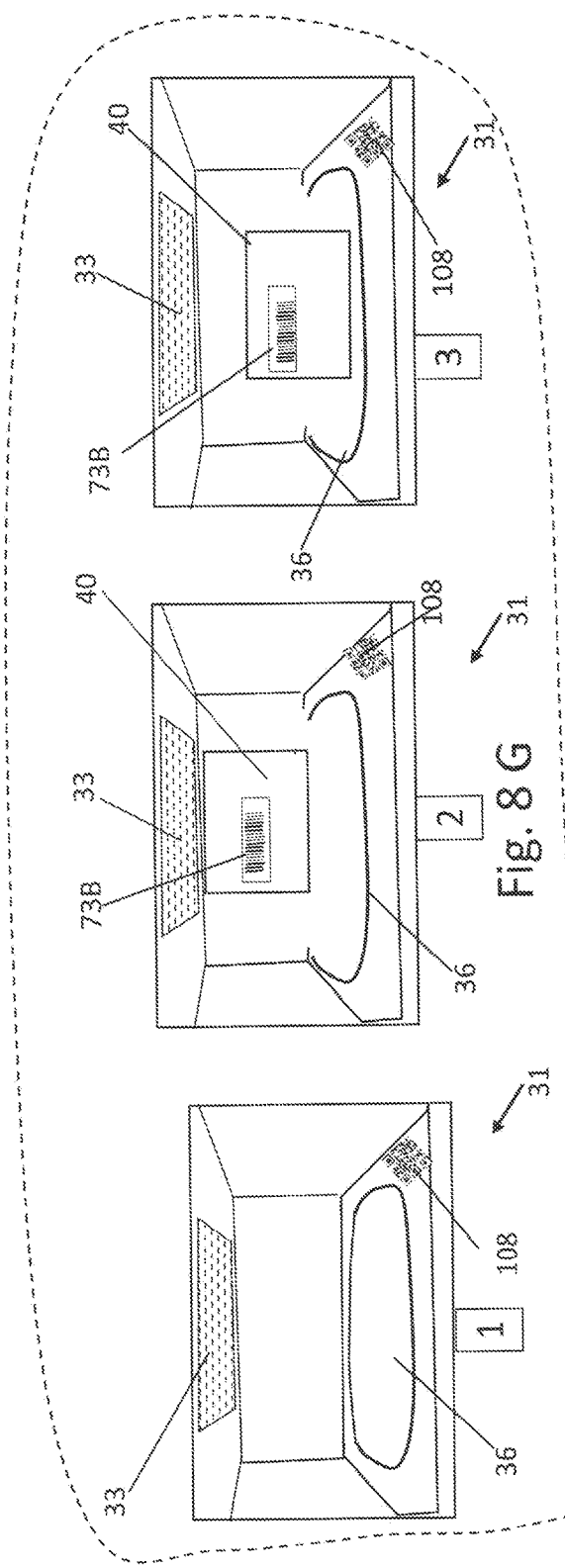
Figure 8:
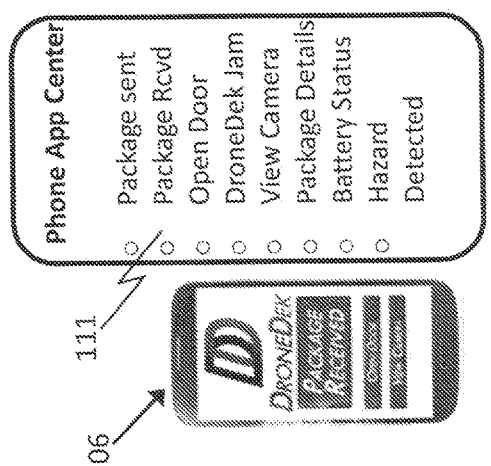

FIG. 8A through 8N are sketches of the operation of delivery by a drone at the residential or commercial receiving location and the expanding DRONEDEK.

FIG. 9A through 9F are sketches of prior art in drone delivery systems to date.

DESCRIPTION OF THE DRAWINGS—REFERENCE NUMERALS

The following list refers to the drawings:

TABLE B

Reference numbers.

| No. | Description |
|---|---|
| 30 | drone docking system/DRONEDEK 30 for deposit of items delivered by drone 50 |
| 31 | drone docking station/DRONEDEK 31 for deposit of items delivered by drone hereinafter referred to as expanded floor/and receiving section drone dock, docking station, the box, or drone box, or docking box) for deposit of items delivered by drone. |
| 31P | prototype 31P of DRONEDEK with extending floor |
| 31DS | design sketches 31DS of DRONEDEK with extending floor |
| 32 | drone docking station structure 32 with expanding section/accordion with a raiseable floor 32F |
| 32A | side and side surface 32A of structure 32 |
| 32B | end and end surface 32B of structure 32 |
| 32C | bottom and bottom surface 32C of structure 32 |
| 32D | control console 32D |
| 32E | clearance 32E for slidable door 34 |
| 32F | raiseable floor 32F of enclosed structure 32 |
| 32FM | motor 32FM to lower floor 32F |
| 32DD | means 32DD to drive floor 32F chain, cable, belt, or the like |
| 32P | pulley/sprocket 32P for means 32DD |
| 32DM | means 32DM to support drive floor 32F at the end where drive means 32DD - enclosed channel, angle with castors or the like |
| 32EM | means 32EM to support drive floor 32F at opposite end of drive - enclosed channel, angle with castors or the like |
| 33 | drone structure/container opening 33 |
| 34 | closeable and openable, movable/motorized sliding doors 34 on the dock structure 32 with a means for heating |
| 34A | door motor 34A |
| 36 | a means 36 to prevent damage and deterioration like a foam or soft padding, a curved side, a sealed door, a temperature-controlled interior, and a heated sliding door. |
| 38 | top surface 38 of docking structure 32 surrounding the perimeter of the opening 34 with a means for heating |
| 39A | mounting pad/foundation plate 39A for structure 32 |
| 40 | parcels 40 such as food items, groceries, tools, electronics, documents, and the like |
| 50 | drone 50 |
| 50A | drone 50A with parcel |
| 50B | drone 50B empty/without parcel |
| 51 | drone pads 51 |

TABLE B-continued

Reference numbers.

| No. | Description |
|---|---|
| 61 | camera system 61 internal/external to compartment of drone 50 having technology and recognition precision to interconnect to various applications for facial recognition of humans and pets |
| 62 | optional receiving dimples 62 for the drone pads 51 |
| 63 | a means of transferring 63 the contents/parcel 40 of the drone 50 to the interior of the box through the opening 34 and a mean of disengaging from the parcel 40 such as controllable arms 64; releasable/locking ball and socket with the package 65; magnetic or electronic holding structure 66 |
| 64 | controllable catch arms 64 or the like |
| 65 | releasable/locking ball and socket with the package 65 or the like |
| 66 | control system 66 for the motors 34A, 32FM, and interface to keyboard 116 |
| 67 | power source 67 |
| 68 | solar panel 68 as a power source |
| 69 | one or more lighting mechanisms 69 inside the container 32 |
| 70 | a means of preserving and securely storing 70 the delivered goods once in the box - i.e., a totally secure solution for home or office drone deliveries of parcels 40 |
| 71 | means for locking 71, a keypad 71A for onsite access to the DRONEDEK, facial recognition or fingerprint |
| 71A | a keypad 71A for onsite access to the DRONEDEK |
| 72 | temperature control 72 hot/cold system |
| 73 | barcode reader 73 - infrared or other |
| 73A | barcode reader waves and signals 73A |
| 73B | barcode reader label 73B on package 40 |
| 74 | wind block 74 |
| 76 | charging station 76 |
| 77 | heated top 77 |
| 78 | a motion flood light 78 that has focus technology to flood an area or create spotlight floods at specific line of sight areas in the yard near the DRONEDEK 31 |
| 79 | mail slot 79 for regular land mail |
| 80 | collector panel 80 for detection of explosives or anthrax or other perceived threats |
| 81 | battery exchange mechanism 81 for interchangeability of drone batteries with the DRONEDEK |
| 82 | extendable/retractable means for exchanging 82 batteries such as an extendable arm and securing latch to remove the drone battery 83, move it to the exchange mechanism 81 and move charged battery 84 back to drone 50 and re-engage the drone power connection |
| 83 | drone battery 83 |
| 84 | charged battery 84 |
| 85 | discharged battery 85 |
| 90 | parcel order mechanism 90 - personal communication devices 106 connected to the network 103 |
| 91 | providing system 91 or goods source - order, supplier, and distribution company - "good stuff company". |
| 92 | external lighting 92 that can be LED type systems to strobe, flash colors, communicate to authorities, distress, etc. |
| 93 | weight and dimension sensors 93 |
| 94 | two-way speakers and loud audio alarm system 94 to communicate to persons at the DRONEDEK 31 or to provide loud alarms, shrill sirens etc. |
| 100 | location and tracking means 100 of all nearby drones and communication with docking station 31 |
| 102 | a means of locating 102 the docking station 31 such that drone can approach and dock with it. GPS system or the like, etc. |
| 103 | cloud/network 103 |
| 104 | satellites 104 |
| 105 | signal and cell towers 105 |
| 106 | personal communication devices 106 - such as smart phones, tablets, laptops, personal computers, and the like |

TABLE B-continued

Reference numbers.

| No. | Description |
|---|---|
| 107 | specific GPS address 107 for the docking station 31 |
| 108 | local signal/or mechanical means 108 - to facilitate final location and transfer such as Cold beam technology, Laser beam, Radar, Lidar, Quick Response (QR) code tags, Radio frequency RFID) remote identification tracking and sensing for drone authentication and landing for navigating the drone 50 to its exact location on the docking station 31 |
| 109 | encrypted signal 109 from the docking station 31 |
| 110 | a means for encrypted communication 110 between the drone and the drone dock, either directly or through a remote server (Wi-Fi, Bluetooth, hot spot, satellite etc. and others) |
| 111 | smart phone application or the like to communicate status of the docking event with the user of the personal communication devices 106 |
| 112 | flight 112 from goods source 91 to docking station 31 |
| 113 | flight 113 from docking station 31 back to good source or another user destination |
| 114 | alternative flight 114 from original docking station to secondary docking station to "pick-up" parcel |
| 115 | Return tattoo printer 115 branding of package for return and ability to place gate code 115A to a codex or manual intervention and delivery |
| 116 | console control keyboard 116 |
| 117 | encrypted anti-theft chips 117 mounted to the frame |
| 120 | micro weather station 120 mechanisms, sensors, etc. |
| 122 | paint and track 122 monitoring communications and follow with GPS once painted |
| 125 | ultraviolet detox/disinfect 125 |
| 130 | ozone detox/disinfect 130 |
| 150 | vault 150 for underground homeowner association installation |
| 151 | structural members 151 for raising platform 155 |
| 152 | rolling sealed top doors 152 |
| 155 | movable platform 155 |
| 156 | open area 156 of vault 150 |
| 157 | means to raise and lower 157 such as chain, cable, rope, belt, and pulleys/sprockets/sheaves connected to motor 158 |
| 158 | means 158 to convert electricity to rotational movement such as electric motor or equal |
| 159 | power source 159 |
| 160 | powered hot/cold plate temperature assist 160 |
| 170 | a set of powered rollers 170 for assist platform 172 |
| 172 | assist platform 172 |
| 175 | extending support arms 175 |
| 177 | extension cylinder 177 for robot/AUVSI assist unit 180 |
| 178 | receptacles 178 for 110 V source, for cellphone charging, and for Tesla, electric scooter, and the like charging |
| 179 | power source 179 for powered rollers and for Tesla, and scooter charging 178 and the like |
| 180 | robot/AUVS (automated unmanned vehicle systems) assist unit 180 to assist unload of parcels 40 to DRONEDEK 31 |
| 400 | prior Art 400 U.S. Pat. No. 9,840,340 to O'Toole in 2017 |
| 401 | prior Art 401 U.S. Pat. No. 10,457,421 to O'Toole in 2019 |
| 402 | prior Art 402 U.S. Pat. No. 10,093,454 to Kalyan in 2018 |
| 403 | prior Art 403 U.S. Pat. No. 9,387,928 to Gentry et al in 2016 |
| 404 | prior Art 404 U.S. Pat. No. 10,124,912 to Walsh in 2018 |
| 405 | prior Art 405 U.S. Pat. No. 9,928,749 to Gil et al in 2018 |

DETAILED DESCRIPTION OF PREFERRED EMBODIMENT

The present development is a Special Expanding Floor/Accordion drone docking station called a DRONEDEK. This invention relates to a Special Expanding Floor/Accordion drone docking station called a DRONEDEK. The invention relates to drones and delivery of parcels or goods.

The present application relates to a delivery location for receiving a package from a vehicle—drone or unmanned aerial vehicle (UAV), robotic carriers, or automated unmanned vehicle systems (AUVS). The present disclosure relates to unmanned and drone aircraft, more specifically to landing and docking systems for unmanned aircraft to deliver o receive goods. The embodiments of the disclosure relate to the field of aircrafts and unmanned vehicular delivery, in particular to a device for receiving and sending an article. A device for a drone docking station for deposit of items delivered by drone, robot or AUVS. Items may include but not be limited to food items, groceries, and parcels. A secure porch, roof, window or otherwise building mounted box may be secured through to an existing edifice or may be configured to mount to an existing mailbox post and/or take the place of the mailbox. The invention relates to drones and delivery of parcels or goods.

The advantages for the Special Expanding Floor/Accordion drone docking station called a DRONEDEK device 30 are listed above in the introduction. Succinctly the benefits are that the device:

1. Has a secure opening and closing door feature that allows the drone to communicate with the station and open and close its cargo doors to receive and ship its contents—means for locking and a keypad for onsite access to the DRONEDEK;
2. Provides expanded volume for several packages and deliveries to the on-docking station that is a secure receptacle designed to hold parcels that are received or that are waiting to be shipped accompanied with a barcode reader, a return tattoo printer for package return and ability to place gate code for manual intervention and delivery;
3. Administers Ultraviolet or ozone disinfecting/detoxing to remove infectious disease, viruses and bacteria;
4. Provides explosive materials and anthrax, etc. detection;
5. Provides inter-communication to other drones, UAVs, AUVS, and robots delivering in the area;
6. Serves as a weather monitoring station, traffic, human and pet movement with facial recognition cameras, as well as able to tag and track for authorities;
7. Interchanges information with providers and collects information for Big Data Collection and Networking for marketing information and data;
8. At the location of the DRONEDEK docking station it provides flood lights, two-way speakers, alarms, and flashing and colored lighting for security and communications;
9. Accommodates a ground vault for meeting homeowner association rules and restrictions;
10. Monitors weight and size of package and can tattoo brand packages for returns;
11. Can provide a charging station or battery exchange to the drones and UAVs;
12. Has an assist mechanism for robot/AUVS (automated unmanned vehicle systems) assist to unload of parcels to DRONEDEK;
13. Has remote access and connectivity with a contents-sensing switch that via its phone application;
14. Has a means of preserving and temperature control for the goods and deliveries of parcels;
15. Has a camera system internal/external to compartment of drone dock with technology and recognition precision to interconnect to applications for facial recognition of humans and pets and paint/tag and track monitoring communications;
16. Is powered by a solar panel and/or 110-volt electrical power supply, allowing for operation of its high-level features and a solar panel as a power source;
17. Protects packages from rain, wind, sleet, hail and snow, and harsh temperatures and a heated cargo door option allows for access during the iciest of weather; and
18. Allows through a GPS beacon for the shipping drone to home in on the DRONEDEK's precise location.

The preferred embodiment of Special Expanding Floor/Accordion drone docking station 31 called a DRONDEK is: A drone dock and delivery box 31 for accepting drone deliveries comprising: (a) a means and structure 32 for expanding the receiving section for containing multiple parcels with a raiseable floor 32F; (b) means of locating 100, 102 the drone dock such that the drone may accurately approach and dock with the drone dock; (c) a means of engaging 51,62 the drone dock 31 such that a stable connection or attachment can be made; (d) a means 63, 64, 65 of transferring the contents 40 of the drone to the interior 33 of the drone dock 31; (e) a means of preserving 70, 72 such as temperature control and a means for securely storing the delivered goods once in the drone dock; (f) a mean of disengaging 51,62 (release) from the drone dock 31; (g) a means of encrypted communication 108, 110 between the drone 50 and the drone dock 31, either directly or through a remote server (Wi-Fi, Bluetooth, hot spot, satellite etc. and others); (h) a set 71, 71A of functional components incorporated within the box to allow for preservation and security of the stored goods, and to prevent damage during the transfer and or subsequent storage (soft); (i) a means of securing 39A the box to a structure at a residential or commercial address 107; (j) a set of optional features comprising a charging station 76 and exchange mechanism 81; a collector 80 to identify explosive material, anthrax and the like; an ultraviolet scan 125 system to eradicate disease, virus and harmful materials; an ozone applicator 130 to eradicate disease, virus and harmful materials; (k) a set of identification feature such as a barcode reader 73, a weight and dimension sensor 93, and a tattoo printer 115 for return parcels; (l) a set of features on the drone dock for weather monitoring 120, tag and track 122 vehicles and packages, etc. and follow with GPS once painted, and a camera 61 with facial recognition software to track humans and pets; and (m) a set of local features such as two-way speakers and loud audio alarms 94, LED light 92 that are colored and can strobe flash, and a flood light 78.

There is shown in FIGS. 1-9 a complete description and operative embodiment of the Special Expanding Floor/Accordion drone docking station called a DRONEDEK device. In the drawings and illustrations, one notes well that the FIGS. 1-9 demonstrate the general configuration and use of this product. The various example uses are in the operation and use section, below.

The accompanying drawings, which are incorporated in and constitute a part of this specification, illustrate an embodiment of the Special Expanding Floor/Accordion drone docking station called a DRONEDEK device 30 that is preferred. The drawings together with the summary description given above and a detailed description given below explain the principles of the DRONEDEK device 30. It is understood, however, that the Special Expanding Floor/Accordion drone docking station called a DRONEDEK device 30 is not limited to only the precise arrangements and instrumentalities shown. Other examples of drone docking stations and package receptacles for drone or unmanned aerial vehicle (UAV), robotic carriers, or automated unmanned vehicle systems (AUVS) to be within the scope and spirit shown here.

FIGS. 1A through 1D are sketches of the general drone docking station/DRONEDEK 31 for deposit of items 40 delivered by drone 50 hereinafter referred to as expanded floor/and receiving section drone dock 31 or docking station. Viewed in these sketches are: a drone docking system/DRONEDEK 30 for deposit of items delivered by drone 50; a drone docking station/DRONEDEK 31 for deposit of items delivered by drone hereinafter referred to as expanded floor/and receiving section drone dock, docking station, the box, or drone box or docking box) for deposit of items delivered by drone; a prototype 31P of DRONEDEK with extending floor; a design sketch 31DS of DRONEDEK with extending floor; and a vault 150 for underground homeowner association installation.

Figure 2:
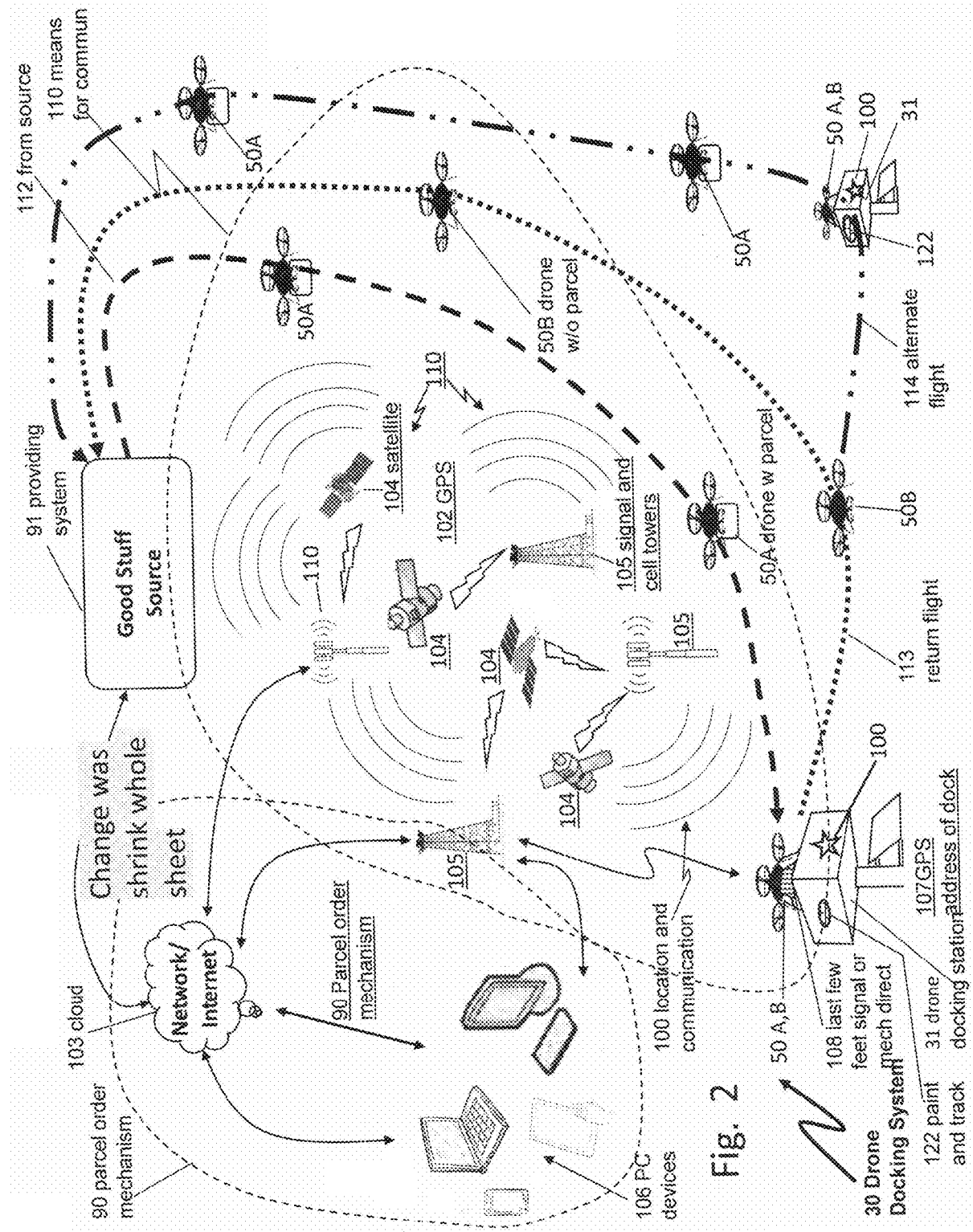
FIG. 2 shows the communication and delivery system from the order of the product/parcel to the delivery to the docking station/DRONEDEK with the expanding section.

FIG. 2 shows the communication and delivery system from the order of the product/parcel to the delivery to the docking station/DRONEDEK with the expanding section. In this view is: a drone docking system/DRONEDEK 30 for deposit of items delivered by drone 50; a drone docking station/DRONEDEK 31 for deposit of items delivered by drone hereinafter referred to as expanded floor/and receiving section drone dock, docking station, the box, or drone box or docking box) for deposit of items delivered by drone; a parcels 40 such as food items, groceries, tools, electronics, documents, and the like; a drone 50; a drone 50A with parcel; a drone 50B empty/without parcel; a parcel order mechanism 90—personal communication devices 106 connected to the network 103; a providing system 91 or goods source—order, supplier, and distribution company—"good stuff company"; a location and tracking means 100 of all nearby drones and communication with docking station 31, 131; a means of locating 102 the docking station 31 such that drone can approach and dock with it. GPS system or the like, etc.; a cloud/network 103; a group of satellites 104; a signal and cell towers 105; a personal communication devices 106—such as smart phones, tablets, laptops, personal computers, and the like; a specific GPS address 107 for the docking station 31; local signal/or mechanical means 108—to facilitate final location and transfer such as Cold beam technology, Laser beam Radar, Lidar, Quick Response (OR) code tags, Radio frequency RFID) remote identification tracking and sensing for drone authentication and landing for navigating the drone 50 to its exact location on the docking station 31; an encrypted signal 109 from the docking station 31; a means for encrypted communication 110 between the drone and the drone dock, either directly or through a remote server (Wi-Fi, Bluetooth, hot spot, satellite etc. and others); a smart phone application 111 or the like to communicate status of the docking event with the user of the personal communication devices 106; a flight 112 from goods source 91 to docking station 31; a flight 113 from docking station 31 back to good source or other user destination; an alternative flight 114 from original docking station to secondary docking station to "pick-up" parcel; and a paint/tag and track 122 monitoring communications and follow with GPS once painted. In the overall control system with the Dronedek receptacles 30, 31, air traffic control data for drone "FAA"—DRONEDEK to utilize drone tracking capabilities and feature. The drone tracking and monitoring features to provide mapping of drone location in and around the geographical area of each DRONDEDEK. Like flightware the drone-ware feature to provide visibility of drones operating in the market including aerial mapping. air traffic control whereby DRONEDEK can schedule incoming and outgoing shipments and can be prioritized by user; marketplace conduit; big data metrics harvesting.

Figure 3A:
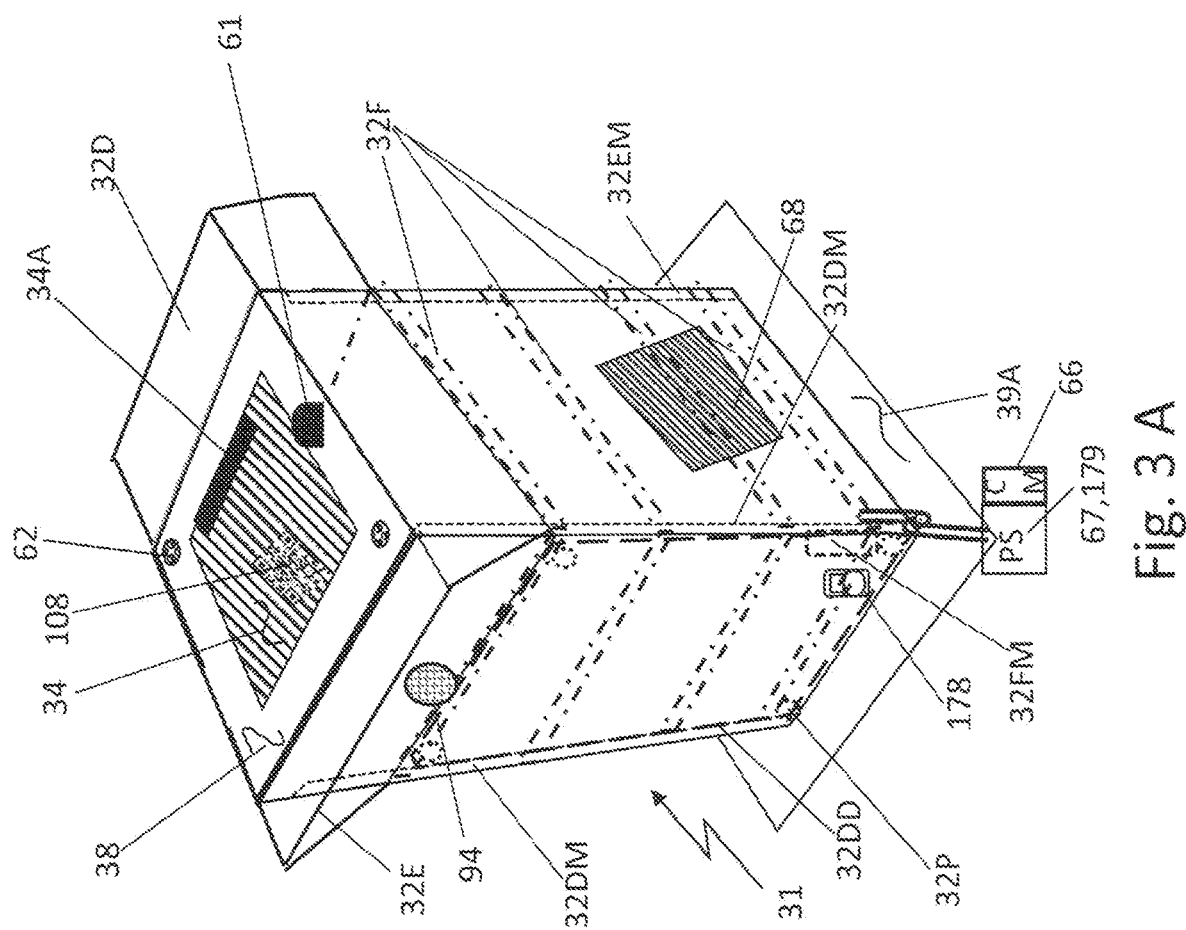

FIGS. 3A through 3C are sketches of a docking station/DRONEDEK 31, 30 with the expanding section 32 with the components and features shown from generally a side or end view. These drawings portray: a drone docking station/DRONEDEK 31 for deposit of items delivered by drone hereinafter referred to as expanded floor/and receiving section drone dock, docking station, the box, or drone box or docking box) for deposit of items delivered by drone; drone docking station structure 32 with expanding section/accordion with a raiseable floor 32F; a side and side surface 32A of structure 32; an end and end surface 32B of structure 32; a bottom and bottom surface 32C of structure 32; a control console 32D; a clearance 32E for slidable door 34; a raiseable floor 32F of enclosed structure 32; a motor 32FM to lower floor 32F; a means 32DD to drive floor 32F chain, cable, belt, or the like; a pulley/sprocket 32P for means 32DD; a means 32DM to support drive floor 32F at the end where drive means 32DD—enclosed channel, angle with castors or the like; a means 32EM to support drive floor 32F at opposite end of drive—enclosed channel, angle with castors or the like; a drone structure/container opening 33; a closeable and openable, movable/motorized sliding door 34 with a means for heating on the dock structure 32; a door motor 34A; a means 36 to prevent damage and deterioration like a foam or soft padding, a curved side, a sealed door, a temperature controlled interior, and a heated sliding door; a top surface 38 of docking structure 32 surrounding the perimeter of the opening 34, the surface 38 with a means for heating; a mounting pad/foundation plate 39A for structure 32; a parcel 40 such as food items, groceries, tools, electronics, documents, and the like; a drone 50; a drone 50A with parcel; a camera system 61 internal/external to compartment of drone 50 having technology and recognition precision to interconnect to applications for facial recognition of humans and pets; an optional receiving dimples 62 for the drone pads 51; a control system 66 for the motors 34A, 32FM, 132FM, 232FM, 332FM, and interface to keyboard 116; an encrypted anti-theft chips 117 mounted to the frame; a power source 67; a solar panel 68 as a power source; a means of preserving and securely storing 70 the delivered goods once in the box—i.e. a totally secure solution for home or office drone deliveries of parcels 40; a temperature control 72 hot/cold system; a barcode reader 73—infrared or other; a temperature control 72 hot/cold system; a barcode reader 73—infrared or other; two-way speakers and loud audio alarm system 94 to communicate to persons at the DRONEDEK 31, 131 or to provide loud alarms, shrill sirens etc.; a console control keyboard 116, receptacles 178 for 110 V source, for cellphone charging, and for Tesla, electric scooter, and the like charging; and power source 179 for powered rollers and for Tesla, and scooter charging 178 and the like.

FIGS. 4A through 4D FIGS. are more sketches of a docking station/DRONEDEK 31 with the expanding section 32 with the components and features shown from several views. Demonstrated in these views are: a drone docking station/DRONEDEK 31 for deposit of items delivered by drone hereinafter referred to as expanded floor/and receiving section drone dock, docking station, the box, or drone box or docking box) for deposit of items delivered by drone; drone docking station structure 32 with expanding section/accordion with a raiseable floor 32F; a side and side surface 32A of structure 32; an end and end surface 32B of structure 32; a bottom and bottom surface 32C of structure 32; a control console 32D; a clearance 32E for slidable door 34 with a means for heating; a raiseable floor 32F of enclosed structure 32; a motor 32FM to lower floor 32F; a means 32DD to drive floor 32F chain, cable, belt, or the like; a pulley/sprocket 32P for means 32DD; a means 32DM to support drive floor 32F at the end where drive means 32DD—enclosed channel, angle with castors or the like; a means 32EM to support drive floor 32F at opposite end of drive—enclosed channel, angle with castors or the like; a drone structure/container opening 33; a closeable and openable, movable/motorized sliding door 34 on the dock structure 32; a door motor 34A; a means 36 to prevent damage and deterioration like a foam or soft padding, a curved side, a sealed door, a temperature controlled interior, and a heated sliding door; a top surface 38 of docking structure 32 surrounding the perimeter of the opening 34 with a means for heating; a mounting pad/foundation plate 39A for structure 32; a parcel 40 such as food items, groceries, tools, electronics, documents, and the like; a drone 50; a drone 50A with parcel; a camera system 61 internal/external to compartment of drone 50 having technology and recognition precision to interconnect to applications for facial recognition of humans and pets; an optional receiving dimples 62 for the drone pads 51; a control system 66 for the motors 34A, 32FM, 132FM, 232FM, 332FM, and interface to keyboard 116; a power source 67; a solar panel 68 as a power source; a means of preserving and securely storing 70 the delivered goods once in the box—i.e. a totally secure solution for home or office drone deliveries of parcels 40; a temperature control 72 hot/cold system; a barcode reader 73—infrared or other; a temperature control 72 hot/cold system; a barcode reader 73 —infrared or other; two-way speakers and loud audio alarm system 94 to communicate to persons at the DRONEDEK 31, 131 or to provide loud alarms, shrill sirens etc.; a return tattoo printer 115 branding of package for return and ability to place gate code 115A to a codex or manual intervention and delivery; a console control keyboard 116; an encrypted anti-theft chips 117 mounted to the frame; receptacles 178 for 110 V source, for cellphone charging, and for Tesla, electric scooter, and the like charging; and a power source 179 for powered rollers and for Tesla, and scooter charging 178 and the like.

FIG. 5 is a group of sketches 31DS and prototype 31P of a docking station/DRONEDEK 31 with the expanding section 32. Shown here are a prototype 31P of DRONEDEK with extending floor and a design sketch 31DS of DRONEDEK with extending floor. These speak for themselves based on the other drawings herein.

FIG. 6A through 6N are sketches of a general embodiment of the expanding DRONEDEK 31 indicating some of the features of the DRONEDEK. Portrayed here are the following: a drone docking station/DRONEDEK 31 for deposit of items delivered by drone hereinafter referred to as expanded floor/and receiving section drone dock, docking station, the box, or drone box or docking box) for deposit of items delivered by drone; a drone docking station structure 32 with expanding section/accordion with a raiseable floor 32F; a drone structure/container opening 33; a closeable and openable, movable/motorized sliding doors 34 on the dock structure 32; a door motor 34A; a means 36 to prevent damage and deterioration like a foam or soft padding, a curved side, a sealed door, a temperature controlled interior, and a heated sliding door; a top surface 38 of docking structure 32 surrounding the perimeter of the opening 34; a parcel 40 such as food items, groceries, tools, electronics, documents, and the like; a drone 50; a camera system 61 internal/external to compartment of drone 50 having technology and recognition precision to interconnect to applications for facial recognition of humans and pets; an optional receiving dimples 62 for the drone pads 51; a releasable/locking ball and socket 65 with the package 40 or the like; one or more lighting mechanisms 69 inside the container 32; a means of preserving and securely storing 70 the delivered goods once in the box—i.e. a totally secure solution for home or office drone deliveries of parcels 40; a temperature control 72 hot/cold system; a barcode reader 73—infrared or other; a barcode reader waves and signals 73A; a barcode reader label 73B on package 40; a wind block 74; a charging station 76; a heated top 77; a motion flood light 78 that has focus technology to flood an area or create spotlight floods at specific line of sight areas in the yard near the DRONEDEK 31, 131; a mail slot 79 for regular land mail; a collector panel 80 for detection of explosives or anthrax or other perceived threats; a battery exchange mechanism 81 for interchangeability of drone batteries with the DRONEDEK; an extendable/retractable means for exchanging 82 batteries such as an extendable arm and securing latch to remove the drone battery 83, move it to the exchange mechanism 81 and move charged battery 84 back to drone 50 and re-engage the drone power connection; a drone battery 83; a charged battery 84; a discharged battery 85; a weight and dimension sensors 93; a two-way speakers and loud audio alarm system 94 to communicate to persons at the DRONEDEK 31, 131 or to provide loud alarms, shrill sirens etc.; a location and tracking means 100 of all nearby drones and communication with docking station 31, 131; a specific GPS address 107 for the docking station 31; a return tattoo printer 115 branding of package for return and ability to place gate code 115A to a codex or manual intervention and delivery; micro weather station 120 mechanisms, sensors, etc.; a paint/tag and track 122 monitoring communications and follow with GPS once painted; an ultraviolet detox/disinfect 125; and an ozone detox/disinfect 130 using O3 as a disinfectant/detox material.

A further description of several of these features is appropriate. On the external cameras 61 they have a facial recognition system is a technology capable of identifying or verifying a person from a digital image or a video frame from a video source. There are multiple methods in which facial recognition systems work, but in general, they work by comparing selected facial features from given image with faces within a database. It is also described as a Biometric Artificial Intelligence based application that can uniquely identify a person by analyzing patterns based on the person's facial textures and shape. While initially a form of computer application, it has seen wider uses in recent times on mobile platforms and in other forms of technology, such as robotics. It is typically used as access control in security systems and can be compared to other biometrics such as fingerprint or eye iris recognition systems. Although the accuracy of facial recognition system as a biometric technology is lower than iris recognition and fingerprint recognition, it is widely adopted due to its contactless and non-invasive process. Recently, it has also become popular as a commercial identification and marketing tool. Other applications include advanced human-computer interaction, video surveillance, automatic indexing of images, and video database, among others.

As to a barcode reader 73, a barcode reader (or barcode scanner) is an optical scanner that can read printed barcodes, decode the data contained in the barcode and send the data to a computer. Like a flatbed scanner, it consists of a light source, a lens and a light sensor translating for optical impulses into electrical signals. Additionally, nearly all barcode readers contain decoder circuitry that can analyze the barcode's image data provided by the sensor and sending the barcode's content to the scanner's output port. Barcode readers can be differentiated by technologies as follows: Pen-type reader consist of a light source and photodiode that are placed next to each other in the tip of a pen. To read a barcode, the person holding the pen must move the tip of it across the bars at a relatively uniform speed. The photodiode measures the intensity of the light reflected from the light source as the tip crosses each bar and space in the printed code. The photodiode generates a waveform that is used to measure the widths of the bars and spaces in the barcode. Dark bars in the barcode absorb light and white spaces reflect light so that the voltage waveform generated by the photodiode is a representation of the bar and space pattern in the barcode. This waveform is decoded by the scanner in a manner like the way Morse code dots and dashes are decoded. The Laser scanners work the same way as pen-type readers except that they use a laser beam as the light source and typically employ either a reciprocating mirror or a rotating prism to scan the laser beam back and forth across the barcode. As with the pen-type reader, a photodiode is used to measure the intensity of the light reflected from the barcode. In both pen readers and laser scanners, the light emitted by the reader is rapidly varied in brightness with a data pattern and the photodiode receive circuitry is designed to detect only signals with the same modulated pattern. CCD readers use an array of hundreds of tiny light sensors lined up in a row in the head of the reader. Each sensor measures the intensity of the light immediately in front of it. Each individual light sensor in the CCD reader is extremely small and because there are hundreds of sensors lined up in a row, a voltage pattern identical to the pattern in a barcode is generated in the reader by sequentially measuring the voltages across each sensor in the row. The important difference between a CCD reader and a pen or laser scanner is that the CCD reader is measuring emitted ambient light from the barcode whereas pen or laser scanners are measuring reflected light of a specific frequency originating from the scanner itself. LED scanners can also be made using CMOS sensors, and are replacing earlier Laser-based readers.

For a collector panel 80: An explosives trace-detection portal machine, also known as a trace portal machine and commonly known as a puffer machine, is a security device that seeks to detect explosives and illegal drugs at airports and other sensitive facilities as a part of airport security screening. The machines are intended as a secondary screening device, used as a complement to, rather than a substitute for, traditional X-ray machines. The term "trace-detection" refers to the machine's ability to detect extremely small "traces" of these compounds. The exact sensitivities of these machines are not available information, but a mass spectrometer detects compounds on a molecular level and would only be limited by the efficiency of the collection from the air puffed to obtain a sample for analysis. Some companies use ion mobility spectrometry (IMS) technology and can detect explosives such as RDX, PETN, TNT, and Nitroglycerin. It can also detect controlled substances such as marijuana, cocaine, heroin, PCP, methamphetamine, and MDMA. One system developed is physically similar but internally different. It uses mass spectrometry (MS) technology, which can detect 16 explosive compounds with 10-100× more sensitivity than IMS, resolve multiple compounds at the same time, and perform shoe bomb detection without removing shoes. This collection technology is also significantly different and offers a narcotics screening portal as a separate product. The machine operates by releasing multiple puffs of air at a passenger who is standing upright within the machine. This will flush out any particles on the person inside the machine then analyze and identify them in seconds. It is capable of screening up to 180 passengers an hour. This sample is then analyzed using IMS or MS technology to search for specific explosive or narcotic compounds. If a substance of concern is detected, the security personnel are notified by a visible and/or audible alarm. The machine can also be used for other bio-hazardous materials associated but not limited to bio- and germ-warfare chemicals and biological hazards.

For a micro weather station 120 mechanisms, sensors, etc. consider this background: Used is a novel and practical micro weather station, which can sense temperature, relative humidity, pressure, and anemometer, and is portable in small size and possesses high precisions. The micro weather station comprises multi-sensor chip, anemometer, measurement system, display system and power management system. Based on MEMS technology, multi-sensor chip integrated temperature, relative humidity and pressure is developed and manufactured. A drag force wind sensor using the torque of cantilever to measure the velocity of wind is developed. The wind direction can be measured by perpendicularly encapsulating the two-wind sensor. Compared with those processes used in other types of micro weather station, the processes used is very simple and compatible. All the results exhibit outstanding performances of the micro weather station. Micro-electromechanical systems (MEMS) are a process technology used to create tiny integrated devices or systems that combine mechanical and electrical components. They are fabricated using integrated circuit (IC) batch processing techniques and can range in size from a few micrometers to millimeters. Weather monitoring is of great importance in many domains such as: agriculture, military, entertainment etc. There are several solutions for monitoring the weather. The classical solution consists in static weather stations. Another solution is based on wireless sensor networks (WSNs). The third solution uses low dimensions weather stations. This paper presents a weather station made of temperature, humidity, pressure, and luminosity sensors embedded in a microcontroller-based board. The station is controlled through the SMS service of mobile phones. Weather sensors from micro systems companies are redefining what an all-in-one weather sensor should be. Everything needed for weather sensing is built into one unit. That includes 27 environmental parameters, a processor, communications unit, and solar power system. Small and lightweight, these portable weather sensors take on jobs previously reserved for larger, more complex systems. Within 60 seconds of turning them on, they are ready to transmit local conditions using a cellular or Iridium satellite link. With these advantages in size, weight and ruggedness, weather sensors are opening new markets and locations for autonomous meteorological sensors. Typical desires for a weather stations include (for example and not as a limitation): Cloud-based data logging, solar power, and processor; Two-way Cellular or Iridium satellite connection; integrated panoramic imaging; Expansion port; Rugged and portable; Easy installation; and Autonomous operations. The Weather Data Collected is typically: Temperature; Barometric pressure; Humidity; Wind speed; Wind direction; Compass reading; Angular tilt; Visibility; Dust accumulation; Lightning distance; Visual imagery; Precipitation amount; Present weather; and GPS location.

A Paint/tag and track 122 monitoring communications considers this: Drones 50 and these docking stations 31 can tag and track quarry using nanoparticle sprays. The US Air Force is funding work to let drones to tag suspects or cars with a spray that gives them a distinct spectral signature, making them easy to track. On a dusty road in northern Pakistan, a nondescript vehicle rounds a corner. Fifty meters overhead, a tiny drone buzzes unseen, spraying a fine mist across the vehicle's roof as it passes below. The vehicle is now tagged and can be tracked from many kilometers away by an infrared scanner on a larger drone. This scenario may soon be played out now that the US Air Force has contracted to develop a drone-based tagging system. Tagging materials—taggants—are made that can be used to discreetly label vehicles carrying smuggled goods, or people who are involved in civil disobedience or attempting to cross international borders illegally. Interest in tagging technology has been driven in part by growing pressure on the White House over civilian deaths in US drone attacks. Tagging by drones would allow people to be tracked for subsequent arrest. Some taggants are based on quantum dots—semiconductor nanocrystals less than 50 atoms across. Because of quantum effects, they absorb and emit light at specific wavelengths. The company has demonstrated a taggant powder that, when illuminated with an invisible ultraviolet laser, can be detected by infrared cameras 2 kilometers away. The powder is delivered as an aerosol that clings to metal, glass and cloth, and batches can be engineered to have distinct spectral signatures. The nanocrystals would be sprayed by a hand-launched drone with a wingspan of less than 1.5 meters, it is quiet and has a range of several kilometers. A larger Predator drone could then illuminate the target with an ultraviolet laser and track its progress. "Nanocrystals can be sprayed by a hand-launched drone and illuminated with a laser". But spraying the taggant accurately can be tricky. They experimented with small drones that delivered a simulated taggant made from colored sugar beads used in cake decoration. They wanted to coat a road with the stuff so that it would stick to the wheels of any vehicle that drove through. But the wind blew the beads around as soon as they were sprayed. So, the team developed software to model the effects of wind so they could allow for it when spraying When they fed in estimates of wind speed and direction based on readings from the drone's sensors, the drone could hit a target from an altitude of 45 meters. A more advanced system would allow accurate tagging from greater distances, which would be more effective as small drones can be inaudible when flying further than 60 meters away. The US Department of Homeland Security has expressed interest in giving non-lethal offensive capabilities to drones used by its Customs and Border Protection service. Any such move is bound to be contentious, and tagging might prove more acceptable to US public opinion. Drones could also use smart tagging during riots so that the people involved can be identified and later arrested. Many ways to make one's mark—TAGGING technology has moved on since the days of using water cannon with indelible dye to mark rioters. One company produces a range of products containing unique synthetic DNA sequences. These include automatic sprays for marking intruders, a personal defense spray and a device like a paintball pistol that can tag an individual from 30 meters away. Once painted they can follow the items with GPS.

For Ultraviolet detox/disinfect 125 systems: Ultraviolet germicidal irradiation (UVGI) is a disinfection method that uses short wavelength ultraviolet (ultraviolet C or UVC), light to kill or inactivate microorganisms by destroying nucleic acids and disrupting their DNA, leaving them unable to perform vital cellular functions. UVGI is used in a variety of applications, such as food, air, and water purification. UVC light is weak at the Earth's surface as the ozone layer of the atmosphere blocks it. UVGI devices can produce strong enough UVC light in circulating air or water systems to make them inhospitable environments to microorganisms such as bacteria, viruses, molds, and other pathogens. UVGI can be coupled with a filtration system to sanitize air and water. The application of UVGI to disinfection has been an accepted practice since the mid-20th century. It has been used primarily in medical sanitation and sterile work facilities. Increasingly, it has been employed to sterilize drinking and wastewater, as the holding facilities are enclosed and can be circulated to ensure a higher exposure to the UV. In recent years UVGI has found renewed application in air purifiers. UV light is electromagnetic radiation with wavelengths shorter than visible light but longer than X-rays. UV is categorized into several wavelength ranges, with short-wavelength UV (UVC) considered "germicidal UV". Wavelengths between about 200 nm and 300 nm are strongly absorbed by nucleic acids. The absorbed energy can result in defects including pyrimidine dimers. These dimers can prevent replication or can prevent the expression of necessary proteins, resulting in the death or inactivation of the organism.

Mercury-based lamps operating at low vapor pressure emit UV light at the 253.7 nm line.

Ultraviolet light-emitting diodes (UVC LED) lamps emit UV light at selectable wavelengths between 255 and 280 nm.

Pulsed-xenon lamps emit UV light across the entire UV spectrum with a peak emission near 230 nm.

Microorganisms have less protection against UV and cannot survive prolonged exposure to it. A UVGI system is designed to expose environments such as water tanks, sealed rooms and forced air systems to germicidal UV. Exposure comes from germicidal lamps that emit germicidal UV at the correct wavelength, thus irradiating the environment. The forced flow of air or water through this environment ensures exposure. The degree of inactivation by ultraviolet radiation is directly related to the UV dose applied to the water. The dosage, a product of UV light intensity and exposure time, is usually measured in microjoules per square centimeter, or equivalently as microwatt seconds per square centimeter ($was/cm^2$). Dosages for a 90% kill of most bacteria and viruses range from 2,000 to 8,000 $was/cm^2$. Larger parasites such as *cryptosporidium* require a lower dose for inactivation. As a result, the U.S. Environmental Protection Agency has accepted UV disinfection as a method for drinking water plants to obtain *cryptosporidium*, giardia, or virus inactivation credits. For example, for a 90% reduction of *cryptosporidium*, a minimum dose of 2,500 $pW \cdot s/cm^2$ is required based on the U.S. EPA UV Guidance Manual published in 2006. The effectiveness of germicidal UV depends on the length of time a microorganism is exposed to UV, the intensity and wavelength of the UV radiation, the presence of particles that can protect the microorganisms from UV, and a microorganism's ability to withstand UV during its exposure. In many systems, redundancy in exposing microorganisms to UV is achieved by circulating the air or water repeatedly. This ensures multiple passes so that the UV is effective against the highest number of microorganisms and will irradiate resistant microorganisms more than once to break them down. "Sterilization" is often misquoted as being achievable. While it is theoretically possible in a controlled environment, it is very difficult to prove, and the term "disinfection" is generally used by companies offering this service as to avoid legal reprimand. Specialist companies will often advertise a certain log reduction, e.g., 6-log reduction or 99.9999% effective, instead of sterilization. This takes into consideration a phenomenon known as light and dark repair (photoreactivation and base excision repair, respectively), in which a cell can repair DNA that has been damaged by UV light. The effectiveness of this form of disinfection depends online-of-sight exposure of the microorganisms to the UV light. Environments where design creates obstacles that block the UV light are not as effective. In such an environment, the effectiveness is then reliant on the placement of the UVGI system so that line of sight is optimum for disinfection. Dust and films coating the bulb lower UV output. Therefore, bulbs require periodic cleaning and replacement to ensure effectiveness. The lifetime of germicidal UV bulbs varies depending on design. Also, the material that the bulb is made of can absorb some of the germicidal rays.

For Ozone detox/disinfect unit 130 utilizing O3 to disinfect: Microorganisms cause issues in various places, in a clinical setting bacterium can cause dangerous outbreaks. Ozone can be used as a chemical disinfectant to kill bacteria and viruses with low ozone concentrations. The contact time is altered depending on the desired deactivation grade. For many applications, a bacteria reduction of 99.99% which corresponds to a 4-log reduction is enough, for a higher deactivation grade the solution is easily adapted to provide higher concentrations and exposure time, in adapted solutions even bacteria spores can be treated. The figure above applies for treatment in rooms and ventilation ducts, that have been used with ozone to limit the spread of airborne microorganisms in food industries and food storage. Non-touch technologies include the usage of UV-lamps and chemicals dispersed as an aerosol or gas which deactivates microorganisms. Compared to other treatment methods for air disinfection, ozone can efficiently disinfect large air volumes, neutralizing microorganisms, including viruses. This makes it ideal for use in medical applications, for example in hospitals or doctors waiting rooms. An important factor that enables savings is the time the cleaning agent can actively deactivate bacteria. Ozone concentration is adapted to the desired log reduction after finished treatment ozone either decompose into oxygen naturally over several hours or the decomposition is accelerated significantly using ozone destructors.

FIG. 7A through 7E are sketches of an inground vault system 150 for homeowner associations and an assist mechanism 180 for unloading robot/AUVS (automated unmanned vehicle systems). Demonstrated by these drawings are a drone docking station/DRONEDEK 31 for deposit of items delivered by drone hereinafter referred to as expanded floor/and receiving section drone dock, docking station, the box, or drone box, or docking box) for deposit of items delivered by drone; a control system 66 for the motors 34A, 32FM, 132FM, 232FM, 332FM, and interface to keyboard 116; a vault 150 for underground homeowner association installation; a structural member 151 for raising platform 155; a rolling sealed top doors 152; a movable platform 155; an open area 156 of vault 150; a means to raise and lower 157 such as chain, cable, rope, belt, and pulleys/sprockets/sheaves connected to motor 158; a means 158 to convert electricity to rotational movement such as electric motor or equal; a power source 159; a set of powered rollers 170 for assist platform 172; an assist platform 172; an extending support arms 175; an extension cylinder 177 for robot/AUVSI assist unit 180; a receptacles 178 for 110 V source, for cellphone charging, and for Tesla, electric scooter, and the like charging; a power source 179 for powered rollers and for Tesla, and scooter charging 178 and the like; a robot/AUVS (automated unmanned vehicle systems) assist unit 180 to assist unload of parcels 40 to DRONEDEK 31, 131; and a motor and hydraulic unit 332FK to robot/AUVSI assist unit 180.

FIG. 8A through 8N are sketches of the operation of delivery by a drone 50 at the residential or commercial receiving location 107 and the expanding DRONEDEK 31. This section is described below in the Operations Section.

FIG. 9A through 9F are sketches of prior art in drone delivery systems to date. Here former patents and applications for various docking station and systems are shown. These include: a prior art 400 U.S. Pat. No. 9,840,340 to O'Toole in 2017 named Drone docking station and delivery system; a prior art 401 U.S. Pat. No. 10,457,421 to O'Toole in 2019 named a Drone docking station and delivery system; a prior art 402 U.S. Pat. No. 10,093,454 to Kalyan in 2018 entitled a Unmanned aerial vehicle payload receiving apparatus; a prior art 403 U.S. Pat. No. 9,387,928 to Gentry et al in 2016 called a Multi-use UAV docking station systems and methods; a prior art 404 U.S. Pat. No. 10,124,912 to Walsh in 2018 called a Landing pad for unmanned aerial vehicle delivery; and a prior art 405 U.S. Pat. No. 9,928,749 to Gil et al in 2018 entitled Methods for delivering a parcel to a restricted access area. As can be seen, the Special Expanding Floor/Accordion drone docking station 31 called a DRONEDEK device is a unique combination and use as described herein.

The objects include, but are not limited to:

Objects: 1. To provide for communication between the drone dock and a drone, 2. To provide security, and preservation of the delivered goods before during and after delivery, and 3. To provide expansion of the secure retention area for accepting several deliveries.

Features include:

| | |
|---|---|
| Security | Has a secure opening and closing door feature that allows the drone to communicate with the station and open and close its cargo doors to receive and ship its contents - means for locking 71 and a keypad 71A for onsite access to the DRONEDEK. |
| Expanding receiver | Provides expanded volume for several packages and deliveries to the on-docking station. |
| Protection from explosions, disease, etc. | collector panel 80 for detection of explosives or anthrax or other perceived threats. |
| Weather data station | micro weather station 120 mechanisms, sensors, etc. |
| Intercommunications with drones and UAV | location and tracking means 108, 100, 110 of all nearby drones and communication with docking station 31. Able to have encrypted communication and tracking of driverless vehicles, robots, vendors that interact with drones. DRONEDEK to utilize non station drone delivery features including vehicle and commercial carriers and mobile DRONEDEK applications; provides the ability to track and interface with aerial, driverless cars or robots (i.e., full UAV, drone and robotic interface) |
| Data retrieval | Interchanges information with providers and collects information for Big Data Collection and Networking for marketing information and data. |
| Disease and virus removal | ozone detox/disinfect 130 and ultraviolet detox/disinfect 125. |
| Tracking assist | camera system 61 internal/external to compartment of drone 50 having technology and recognition precision to interconnect to applications for facial recognition of humans and pets and paint/tag and track 122 monitoring communications and follow with GPS once painted. |

| | |
|---|---|
| Underground vault | vault 150 for underground homeowner association installation. |
| Assist to unload | robot/AUVS (automated unmanned vehicle systems) assist unit 180 to assist unload of parcels 40 to DRONEDEK 31. |
| Preservation | a means of preserving and securely storing 70 the delivered goods once in the box - i.e., a totally secure solution for home or office drone deliveries of parcels 40 and a temperature control 72 hot/cold system. |
| Local Security Features | At the location of the DRONEDEK docking station 31 it provides flood lights, two-way speakers, dog whistle, loud audio alarms 94, and flashing and colored LED lighting 92 for security and communications and alerting emergency vehicles and first responders. |
| Weather-proof | Protects packages from rain, wind, sleet, hail and snow, and harsh temperatures. A heated cargo door option allows for access during the iciest of weather. |
| GPS Location Enabled | Allows through a GPS beacon for the shipping drone to home in on the DRONEDEK's precise location. |
| Charging Station | Features a built-in charging station that can re-energize the drone, effectively doubling drone delivery range - charging station 76 and battery exchange mechanism 81 for interchangeability of drone batteries with the DRONEDEK. |
| Solar Powered | Is powered by a solar panel and/or 110-volt electrical power supply, allowing for operation of its high-level features - solar panel 68 as a power source. |
| Drop Off and Pick Up | Is a secure receptacle designed to hold parcels that are received or that are waiting to be shipped - a weight and dimension sensors 93, a barcode reader 73 - infrared or other, and a return tattoo printer 115 branding of package for return and ability to place gate code 115A to a codex or manual intervention and delivery, can mark a gate code 115A onto the carton 40 for manual delivery. |
| Flexible installation | Has a secure mounting 39A infrastructure for iron-clad installation to a structure or concrete flat surface. |
| Connectivity | Allows the user to easily stay connected to his/her package. DRONEDEK features a contents-sensing switch that via its app, can communicate successful receipt and shipping of parcels to shipper, recipient, and/or shipping company. A user can even see the package via DRONEDEK's built-in camera 61. |
| Remote Access | Features a secure mobile application allowing for remote camera access and the ability to lock and unlock ones DRONEDEK via one's phone or tablet. The owner of the box may retrieve the contents easily through a simple code entered, key or cell phone application 111. |

The Big Data Collection anticipates using blockchain technology. A simple explanation of this is that a block in a blockchain is a collection of data. The data is added to the block in blockchain, by connecting it with other blocks in chronological others creating a chain of blocks linked together. The first block in the Blockchain is called Genesis Block. A blockchain is a decentralized, distributed and public digital ledger that is used to record transactions across many computers so that any involved record cannot be altered retroactively, without the alteration of all subsequent blocks. A blockchain has been described as a value-exchange protocol. See: https://coingeek.com/ibm-patent-takes-on-package-drone-theft-with-blockcha. With the paint/tag and track 122, camera system 61, collector panel 80, GPS location 107, and data track 108 features and resultant data, by providing the data from the Dronedek receptacles and connecting the receptacles data reservoir to various emergency systems and application, the proper authorities can be alerted and assisted to report emergency events and can help direct/guide authorities to building locations or even locations of vehicles and persons.

The details mentioned here are exemplary and not limiting. Other specific components and manners specific to describing a Special Expanding Floor/Accordion drone docking station called a DRONEDEK device 31,30 may be added as a person having ordinary skill in the field of the art of drone docking station and package receptacles for drone or unmanned aerial vehicle (UAV), robotic carriers, or automated unmanned vehicle systems (AUVS) devices and their uses well appreciates.

OPERATION OF THE PREFERRED EMBODIMENT

The Special Expanding Floor/Accordion drone docking station called a DRONEDEK 31,30 has been described in the above embodiment. The manner of how the device operates is described below. One notes well that the description above and the operation described here must be taken together to fully illustrate the concept of the Special Expanding Floor/Accordion drone docking station called a DRONEDEK 31,30. The preferred embodiment of Special Expanding Floor/Accordion drone docking station 31 called a DRONDEK is: A drone dock and delivery box 31 for accepting drone deliveries comprising: (a) a means and structure 32 for expanding the receiving section for containing multiple parcels with a raiseable floor 32F; (b) means of locating 100, 102 the drone dock such that the drone may accurately approach and dock with the drone dock; (c) a means of engaging 51,62 the drone dock 31 such that a stable connection or attachment can be made; (d) a means 63, 64, 65 of transferring the contents 40 of the drone to the interior 33 of the drone dock 31; (e) a means of preserving 70, 72 such as temperature control and a means for securely storing the delivered goods once in the drone dock; (f) a mean of disengaging 51,62 (release) from the drone dock 31; (g) a means of encrypted communication 108, 110 between the drone 50 and the drone dock 31, either directly or through a remote server (Wi-Fi, Bluetooth, hot spot, satellite etc. and others); (h) a set 71, 71A of functional components incorporated within the box to allow for preservation and security of the stored goods, and to prevent damage during the transfer and or subsequent storage (soft); (i) a means of securing 39A the box to a structure at a residential or commercial address 107; (j) a set of optional features comprising a charging station 76 and exchange mechanism 81; a collector 80 to identify explosive material, anthrax and the like; an ultraviolet scan 125 system to eradicate disease, virus and harmful materials; an ozone applicator 130 to eradicate disease, virus and harmful materials; (k) a set of identification feature such as a barcode reader 73, a weight and dimension sensor 93, and a tattoo printer 115 for return parcels; (l) a set of features on the drone dock for weather monitoring 120, tag and track 122 vehicles and packages, etc. and follow with GPS once painted, and a camera 61 with facial recognition software to track humans and pets; and (m) a set of local features such as two-way speakers and loud audio 94, LED light 92 that are colored and can strobe flash, and a flood light 78.

Special Expanding Floor/Accordion drone docking station called a DRONEDEK 31,30 operates as follows: A secure encrypted code 110 that drone 50 accesses to direct the dock to open its top 34 to allow for safe delivery into the box 31 may be employed. In lieu of code drone may trigger opening of drone dock by simply accessing its landing base. Final communication between the drone and the drone dock 31 may be through electronic or magnetic connection that is made upon the drone landing and connecting with the box.

The communication may be directly between the docking or delivery box and the drone itself upon docking in order to facilitate the transmission of a code in a lock box. In alternative embodiments a remote server may be employed whereby the drone communicates its location and docking details to the remote server, upon which the remote server pings or otherwise delivers and signal directly to the box or an associated IP address triggering it to unlock and open. The box may also communicate via RFID in order to identity itself to the drone (or vice versa) and communicate a bar code or I.D. sequence required for docking and unlocking. In similar fashion a Bluetooth signal may be employed to communicate a code to the drone once the drone is in range of the box and its blue tooth signal. In certain embodiments the box will deliver GPS guidance to the drone for proper docking and delivery into box. Upon successful deposit in the dock, the top will close securely assuring that entry into the dock by vandals, thieves or animals is prohibited. Retrigger to close may be accomplished in similar fashion to the signal to open either by direct communication between the drawing and the box or through a remote server. The box may also be designed to automatically close and lock once the drone un-docks from the box. And the communication may also be turn over a wireless network such as Wi-Fi, Bluetooth, satellite etc. and others that would be recognized by those skilled in the art. The communication may be directly between the docking or delivery box and the drone itself upon docking to facilitate the transmission of a code in a lock box. In alternative embodiments a remote server may be employed whereby the drone communicates its location and docking details to the remote server, upon which the remote server pings or otherwise delivers and signal directly to the box or an associated IP address triggering it to unlock and open. The box may also communicate via RFID to identity itself to the drone (or vice versa) and communicate a bar code 73 or I.D. sequence required for docking and unlocking. In similar fashion a Bluetooth signal may be employed to communicate a code to the drone once the drone is in range of the box and its blue tooth signal. In certain embodiments the box will deliver GPS guidance to the drone for proper docking and delivery into box. Upon successful deposit in the dock, the top will close securely assuring that entry into the dock by vandals, thieves or animals is prohibited. Retrigger to close may be accomplished in similar fashion to the signal to open either by direct communication between the drawing and the box or through a remote server. The box may also be designed to automatically close and lock once the drone un-docks from the box.

The box design may allow a drop of the item 40 into its cavity 33 and onto a floor 32F or pad 36 once the lid 34. The item 40 will drop in and the lid 34 will return to their home position and not allow for access to the inserted item except by the intended recipient. The Drone Dock 31, 30 will then report to its owner and the shipper and the shipping company that the item is securely in the dock and come and retrieve it. The drone dock 31 may also report charging status as well as takeoff status to shipper.

FIG. 8A through 8N are sketches of the operation of delivery by a drone 50 at the residential or commercial receiving location 107 and the expanding DRONEDEK 31. Shown here are: a drone docking station/DRONEDEK 31 for deposit of items delivered by drone hereinafter referred to as expanded floor/and receiving section drone dock, docking station, the box, or drone box or docking box) for deposit of items delivered by drone; a design sketch 31DS of DRONEDEK with extending floor; a drone structure/ container opening 33; a closeable and openable, movable/ motorized sliding doors 34 on the dock structure 32; a foam or soft padding 36; a parcel 40 such as food items, groceries, tools, electronics, documents, and the like; a drone 50; a camera system 61 internal/external to compartment of drone 50 having technology and recognition precision to interconnect to applications for facial recognition of humans and pets; an optional receiving dimples 62 for the drone pads 51; a solar panel 68 as a power source; a barcode reader 73—infrared or other; a barcode reader waves and signals 73A; a barcode reader label 73B on package 40; a wind block 74; an external lighting 92 that can be LED type systems to strobe, flash colors, communicate to authorities, distress, etc.; a personal communication devices 106—such as smart phones, tablets, laptops, personal computers, and the like; a specific GPS address 107 for the docking station 31; local signal/or mechanical means 108—to facilitate final location and transfer such as Cold beam technology, Laser beam, Radar, Lidar, Quick Response (QR) code tags, Radio frequency RFID) remote identification tracking and sensing for drone authentication and landing for navigating the drone 50 to its exact location on the docking station 31; and a smart phone application 111 or the like to communicate status of the docking event with the user of the personal communication devices 106. Shipping and receiving by the drones are Coordinated with the FAA, sender and receiver of the goods 91 when a package is sent or received. Any conflicts send an indicator/warning signal to the smart phone (FIG. 8H) as well as when items are being received and shipped. If a problem occurs for receiving such as an oversize package or full receptacle 30,31, a message is sent and the package is sent to a pre-arranged overflow zone. Every Dronedek receptacle 30,31 has what is called the drone zone which is an overflow area for items that are too large or non-functioning DroneDek or that a receptacle is full and there is an electronic surveillance at the zone which monitors packages dropped in those areas. The client is notified that the package is there and if somebody breaks that field and takes that item there is a photo/video and electronic visual documentation of that person. At the zone, an audible alarm "warning one that he/she is too close to the package, please step back or the alarm will sound" is present like the Viper alarm system RTM for vehicles.

With this description it is to be understood that the Special Expanding Floor/Accordion drone docking station called a DRONEDEK 31, 30 is not to be limited to only the disclosed embodiment of product. The features of the Special Expanding Floor/Accordion drone docking station called a DRONEDEK 31, 30 are intended to cover various modifications and equivalent arrangements included within the spirit and scope of the description.

While certain novel features of this invention have been shown and described and are pointed out in the annexed claims, it is not intended to be limited to the details above, since it will be understood that various omissions, modifications, substitutions and changes in the forms and details of the device illustrated and, in its operation, can be made by those skilled in the art without departing in any way from the spirit of the present invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described above in the foregoing paragraphs.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. Various features and aspects of the disclosed embodiments can be combined with or substituted for one another to form varying modes of the disclosed inventions. Thus, it is intended that the scope of at least some of the present inventions herein disclosed should not be limited by the particularly disclosed embodiments described above.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. Accordingly, the subject matter recited in the claims is not coextensive with and should not be interpreted to be coextensive with any embodiment, feature, or combination of features shown herein. This is true even if only a single embodiment of the feature or combination of features is illustrated and described herein. Thus, the appended claims should be read to be given their broadest interpretation in view of the prior art and the ordinary meaning of the claim terms.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed considering the number of recited significant digits and by applying ordinary rounding techniques.

The present invention contemplates modifications as would occur to those skilled in the art. While the disclosure has been illustrated and described in detail in the figures and the foregoing description, the same is to be considered as illustrative and not restrictive in character, it being understood that only selected embodiments have been shown and described and that all changes, modifications, and equivalents that come within the spirit of the disclosures described heretofore and or/defined by the following claims are desired to be protected.

What is claimed is:

1. A drone dock and delivery box with an expanding/accordian floor for accepting a group of multiple drone deliveries of a goods/parcel to a person requesting a delivery, the drone dock comprising:
   (a) a structure for expanding the receiving section for containing multiple parcels with a raiseable floor and the structure with a motorized sliding door;
   (b) a means for locating the drone dock with GPS and then for permitting the drone to accurately approach and to dock with the station;
   (c) a means of engaging the drone dock such that a stable connection/attachment can be made;
   (d) a means of transferring each of the goods/parcels from the drone to the interior of the structure of the drone dock;
   (e) a means of preserving the predetermined temperature with a powered hot/cold plate and temperature assist and control unit(160);
   (f) a means for securely storing the goods/parcels once to the interior of the structure of the drone dock;
   (g) a means of disengaging/releasing the drone from the drone dock;
   (h) a means of encrypted communication between the drone and the drone dock which has a specific GPS address and communication to the person requesting the delivery of the goods/parcel;
   (i) a set of functional components incorporated within the box to prevent damage and deterioration during the transfer and or subsequent storage;
   (j) a set of optional features;
   (k) a set of identification feature;
   (l) a set of additional features on the drone; and
   (m) a set of local features
   wherein the goods/parcel that is delivered to the person requesting can be tracked and delivered and a set of demographics regarding the tracking and delivery can provide data for a marketing study.

2. The drone dock and delivery box with an expanding/accordian floor in claim 1 wherein the means for securely storing the goods/parcels once transferred to the interior of the structure of the drone dock is selected from the group consisting of a keypad for onsite access to the drone dock, a facial recognition camera, and a fingerprint activated release system.

3. The drone dock and delivery box with an expanding/accordion floor in claim 1 wherein the means for locating the drone dock with GPS and then for permitting the drone to accurately approach and to dock with the station is selected from a group consisting of cold beam technology, laser beam, radar, lidar, Quick Response (QR) code tags, and radio frequency identification (RFID).

4. The drone dock and delivery box with an expanding/accordion floor in claim 1 wherein the means of encrypted communication between the drone and the drone dock is selected from the group consisting of Wi-Fi, Bluetooth, hot spot, and satellite systems and wherein the drone dock has encrypted communication and tracking of a driverless vehicles, a robots, and vendors that interact with the drone dock and wherein the drone dock can track and interface with an aerial drone, a commercial carrier, a driverless car (UAV) and a robot.

5. The drone dock and delivery box with an expanding/accordian floor in claim 1 wherein the functional component to prevent damage and deterioration during the transfer and or subsequent storage is selected from the group consisting of a soft receiving pad, a curved side, a sealed door, a temperature-controlled interior, and a heated sliding door.

6. The drone dock and delivery box with an expanding/accordian floor in claim 1 wherein the optional features are selected from the group consisting of a charging station for drone batteries, an exchange mechanism for a drone battery, a charging station for a cellular telephone, a charging station for an electric scooter, a charging station for an electric bike and a charging station for an electric vehicle.

7. The drone dock and delivery box with an expanding/accordian floor in claim 1 wherein the optional feature is a collector to identify explosive material, biohazards, illegal drugs, and anthrax.

8. The drone dock and delivery box with an expanding/accordian floor in claim 1 wherein the optional feature is an ultraviolet scan system to eradicate disease, virus and harmful materials.

9. The drone dock and delivery box with an expanding/accordian floor claim 1 wherein the optional feature is an ozone applicator to eradicate disease, virus and harmful materials.

10. The drone dock and delivery box with an expanding/accordian floor in claim 1 wherein the set of identification features are a barcode reader and a Quick Response (QR) reader.

11. The drone dock and delivery box with an expanding/accordian floor in claim 1 wherein the set of identification features include a weight and dimension sensor, barcode reader, and QR reader.

12. The drone dock and delivery box with an expanding/accordian floor in claim 1 wherein the set of identification feature is a tattoo printer for reverse logistics and for return of parcels.

13. The drone dock and delivery box with an expanding/accordian floor in claim 1 wherein an additional feature on the drone dock is a weather monitoring system.

14. The drone dock and delivery box with an expanding/accordian floor in claim 1 wherein an additional feature on the drone dock is a paint/tag and track component to track vehicles and packages.

15. The drone dock and delivery box with an expanding/accordian floor in claim 1 wherein an additional feature on the drone dock is a camera with facial recognition software to track humans and pets.

16. The drone dock and delivery box with an expanding/accordian floor in claim 1 wherein an additional feature on the drone dock is an encoded chip track to track a lost drone dock receptacle.

17. The drone dock and delivery box with an expanding/accordian floor in claim 1 wherein the local feature is a set of two-way speakers with a dog whistle and wherein the speakers can emit loud sirens to alert emergency vehicles and first responders.

18. The drone dock and delivery box with an expanding/accordian floor in claim 1 wherein the local feature is a set of LED lights that are colored and can strobe flash and wherein the LED lights can alert emergency vehicles and first responders.

19. The drone dock and delivery box for accepting goods/parcels in claim 1 wherein the local feature is a flood light.

20. An inground vault (150) for underground homeowner association installation drone dock and delivery box for accepting goods/parcels as drone deliveries to a person requesting the goods/parcels with a multiple set of hot and cold sections comprising:
  (a) a structure for providing a hot and cold section with an interior wherein each of the hot or cold section can move/roll to the side and enable the drone dock (131) to separate each good/parcel of a group of multiple goods/parcels with a raiseable floor and to maintain and preserve each of the goods/parcels at a predetermined temperature, and the structure having a motorized sliding door;
  (b) a means for locating the drone dock with GPS and then for permitting the drone to accurately approach and to dock with the station;
  (c) a means of engaging the drone dock such that a stable connection/attachment can be made;
  (d) a means of transferring each of the goods/parcels from the drone to the interior of the structure of the drone dock;
  (e) a means of preserving the predetermined temperature with a powered hot/cold plate and temperature assist and control unit (160);
  (f) a means for securely storing the goods/parcels once transferred to the interior of the structure of the drone dock;
  (g) a means of disengaging/releasing the drone from the drone dock;
  (h) a means of encrypted communication between the drone and the drone dock which has a specific GPS address and communication to the person requesting the delivery of the goods/parcels;
  (i) a functional component incorporated within the box to prevent damage and deterioration during the transfer and subsequent storage;
  (j) a transport unit to carry and transport the drone dock;
  (j) a set of optional features;
  (k) a set of identification features;
  (l) a set of additional features on the drone dock; and
  (m) a set of local features;
  wherein the goods/parcel that is delivered to the person requesting the goods/parcels can be tracked and delivered and a set of demographics regarding the tracking and delivery can provide data for a marketing study.

21. The inground vault drone dock and delivery box for accepting goods/parcels in claim 20 wherein the means for securely storing the goods/parcels once transferred to the interior of the structure of the drone dock is selected from the group consisting of a keypad for onsite access to the drone dock, a facial recognition camera, and a fingerprint activated release system.

22. The inground vault drone dock and delivery box for accepting goods/parcels in claim 20 wherein the mobile drone dock and delivery box for accepting goods/parcels in claim 20 wherein the means for securely storing the goods/parcels once transferred to the interior of the structure of the drone dock is selected from the group consisting of a keypad for onsite access to the drone dock, a facial recognition camera, and a fingerprint activated release system.

23. The inground vault drone dock and delivery box for accepting goods/parcels in claim 20 wherein the means for locating the drone dock with GPS and then for permitting the drone to accurately approach and to dock with the station is selected from a group consisting of cold beam technology, laser beam, radar, lidar, Quick Response (QR) code tags, and radio frequency identification (RFID).

24. The vault drone dock and delivery box for accepting goods/parcels in claim 20 wherein the means of encrypted communication between the drone and the drone dock is selected from the group consisting of Wi-Fi, Bluetooth, hot spot, and satellite systems and wherein the drone dock has encrypted communication and tracking of a driverless vehicles, a robots, and vendors that interact with the drone dock and wherein the drone dock can track and interface with an aerial drone, a commercial carrier, a driverless car (UAV) and a robot.

25. The inground vault drone dock and delivery box for accepting goods/parcels in claim 20 wherein the functional component to prevent damage and deterioration during the transfer and or subsequent storage is selected from the group consisting of a soft receiving pad, a curved side, a sealed door, a temperature-controlled interior, and a heated sliding door.

26. The inground vault drone dock and delivery box for accepting goods/parcels in claim 20 wherein the optional features are selected from the group consisting of a charging station for drone batteries, an exchange mechanism for a drone battery, a charging station for a cellular telephone, a charging station for an electric scooter, a charging station for an electric bike and a charging station for an electric vehicle.

27. The inground vault drone dock and delivery box for accepting goods/parcels in claim 20 wherein the optional feature is a collector to identify explosive material biohazards, illegal drugs, and anthrax.

28. The inground vault drone dock and delivery box for accepting goods/parcels in claim 20 wherein the optional feature is an ultraviolet scan system to eradicate disease, virus and harmful materials.

29. The inground vault drone dock and delivery box for accepting goods/parcels in claim 20 wherein the optional feature is an ozone applicator to eradicate disease, virus and harmful materials.

30. The inground vault drone dock and delivery box for accepting goods/parcels in claim 20 wherein the set of identification feature is a barcode reader.

31. The vault dock and delivery box for accepting goods/parcels in claim 20 wherein the set of identification feature is a weight and dimension sensor.

32. The inground vault drone dock and delivery box for accepting goods/parcels in claim 20 wherein the set of identification feature is a tattoo printer for reverse logistics and for return of parcels.

33. The inground vault drone dock and delivery box for accepting goods/parcels in claim 20 wherein an additional feature on the drone dock is a weather monitoring system.

34. The inground vault drone dock and delivery box for accepting goods/parcels in claim 20 wherein an additional feature on the drone dock is a tag and track component to track vehicles and packages.

35. The inground vault drone dock and delivery box for accepting goods/parcels in claim 20 wherein an additional feature on the drone dock is a camera with facial recognition software to track humans and pets.

36. The inground vault drone dock and delivery box for accepting goods/parcels in claim 20 wherein an additional feature on the drone dock is an encoded chip track to track a lost drone dock receptacle.

37. The inground vault drone dock and delivery box for accepting goods/parcels in claim 20 wherein the local feature is a set of two-way speakers with a dog whistle and wherein the speakers can emit loud sirens to alert emergency vehicles and first responders.

38. The inground vault drone dock and delivery box for accepting goods/parcels in claim 20 wherein the local feature is a set of LED lights that are colored and can strobe flash and wherein the LED lights can alert emergency vehicles and first responders.

39. The inground vault drone dock and delivery box for accepting goods/parcels in claim 20 wherein the local feature is a flood light.

* * * * *